US010053713B2

(12) United States Patent
Pfeffer et al.

(10) Patent No.: US 10,053,713 B2
(45) Date of Patent: Aug. 21, 2018

(54) BIOLOGICAL ALKANE OXIDATION

(71) Applicant: EVONIK DEGUSSA GmbH, Essen (DE)

(72) Inventors: Jan Christoph Pfeffer, Hanau (DE); Thomas Haas, Muenster (DE); Oliver Thum, Ratingen (DE); Frank Erhardt, Bielefeld (DE); Eva Maria Wittmann, Traunreut (DE); Christian Gehring, Marl (DE); Sabine Hafkemeyer, Marl (DE); Thomas Hueller, Marl (DE)

(73) Assignee: EVONIK DEGUSSA GmbH, Essen (DE)

( * ) Notice: Subject to any disclaimer, the term of this patent is extended or adjusted under 35 U.S.C. 154(b) by 592 days.

(21) Appl. No.: 14/363,165

(22) PCT Filed: Nov. 22, 2012

(86) PCT No.: PCT/EP2012/073334
§ 371 (c)(1),
(2) Date: Jun. 5, 2014

(87) PCT Pub. No.: WO2013/083412
PCT Pub. Date: Jun. 13, 2013

(65) Prior Publication Data
US 2015/0044744 A1    Feb. 12, 2015

(30) Foreign Application Priority Data
Dec. 5, 2011   (EP) .................... 11191910

(51) Int. Cl.
| C12P 7/52 | (2006.01) |
| C12P 7/02 | (2006.01) |
| C12P 7/16 | (2006.01) |
| C12P 7/24 | (2006.01) |
| C12P 7/40 | (2006.01) |

(52) U.S. Cl.
CPC ............... *C12P 7/52* (2013.01); *C12P 7/02* (2013.01); *C12P 7/16* (2013.01); *C12P 7/24* (2013.01); *C12P 7/40* (2013.01); *Y02E 50/10* (2013.01)

(58) Field of Classification Search
None
See application file for complete search history.

(56) References Cited

U.S. PATENT DOCUMENTS

| 6,620,970 | B2 | 9/2003 | Schiffer et al. |
| 6,639,108 | B2 | 10/2003 | Schiffer et al. |
| 6,764,671 | B2 | 7/2004 | Haas et al. |
| 6,861,540 | B2 | 3/2005 | Herwig et al. |
| 6,878,836 | B2 | 4/2005 | Haas et al. |
| 7,005,528 | B2 | 2/2006 | Haas et al. |
| 7,030,052 | B2 | 4/2006 | Stochniol et al. |
| 7,049,450 | B2 | 5/2006 | Hofen et al. |
| 7,091,384 | B2 | 8/2006 | Jaeger et al. |
| 7,157,610 | B2 | 1/2007 | Hofen et al. |
| 7,195,748 | B2 | 3/2007 | Jaeger et al. |
| 7,507,862 | B2 | 3/2009 | Stochniol et al. |
| 7,754,778 | B2 | 7/2010 | Knott et al. |
| 7,879,938 | B2 | 2/2011 | Häger et al. |
| 7,923,225 | B2 | 4/2011 | Mueller et al. |
| 8,216,813 | B2 | 7/2012 | Thum et al. |
| 8,349,596 | B2 | 1/2013 | Mueller et al. |
| 8,349,907 | B2 | 1/2013 | Henning et al. |
| 8,372,595 | B2 | 2/2013 | Schaffer et al. |
| 8,378,127 | B2 | 2/2013 | Dingerdissen et al. |
| 8,399,658 | B2 | 3/2013 | Hengstermann et al. |
| 8,404,470 | B2 | 3/2013 | Thum et al. |
| 8,445,720 | B2 | 5/2013 | Hannen et al. |
| 8,486,677 | B2 | 7/2013 | Thum et al. |
| 8,604,227 | B2 | 12/2013 | Petrat et al. |
| 8,703,451 | B2 | 4/2014 | Haas et al. |
| 8,703,993 | B2 | 4/2014 | Hannen et al. |
| 8,796,000 | B2 | 8/2014 | Thum et al. |
| 8,809,576 | B2 | 8/2014 | Schraven et al. |
| 9,000,223 | B2 | 4/2015 | Micoine et al. |
| 9,200,043 | B2 * | 12/2015 | Potter ............... C07K 14/21 |
| 2002/0087036 | A1 | 7/2002 | Haas et al. |
| 2003/0212298 | A1 | 11/2003 | Brasse et al. |
| 2008/0293101 | A1 * | 11/2008 | Peters ............. C12N 9/0036 435/69.1 |
| 2010/0068773 | A1 | 3/2010 | Marx et al. |

(Continued)

FOREIGN PATENT DOCUMENTS

| EP | 0 098 137 | * | 1/1984 | ............... C12P 7/26 |
| WO | WO 2013/024111 A1 | | 2/2013 | |

(Continued)

OTHER PUBLICATIONS

Peterson, J.A., et al., 1968, "Enzymatic omega-oxidation. 3. Purification and properties of rubredoxin, a component of the omega-hydroxylation system of Pseudomonas oleovorans", Journal of Biological Chemistry, vol. 243, No. 2, pp. 329-334.*

Ruettinger, R.T., et.al., 1977, "Characterization of the ω-hydroxylase of Pseudomonas oleovorans as a nonheme iron protein", Archives of Biochemist and Biophysics, vol. 183, No. 2 pp. 528-537.*

Kok, M., et al., 1989, "The Pseudomonas oleovorans alkBAC operon encodes two structurally related rubredoxins and an aldehyde dehydrogenase", Journal of Biological Chemistry, vol. 264, No. 10, pp. 5442-5451.*

Eggink, G., et al., 1990, "Rubredoxin reductase of Pseudomonas oleovorans. Structural relationship to other flavoprotein oxidoreductases based on one NAO and two FAD fingerprints", Journal of Molecular Microbiology, vol. 212, pp. 135-142.*

(Continued)

*Primary Examiner* — Anand U Desai
(74) *Attorney, Agent, or Firm* — Oblon, McClelland, Maier & Neustadt, L.L.P.

(57) ABSTRACT

The invention relates to a method for oxidizing an alkane, comprising contacting the alkane with a type alkB oxidoreductase and using a type alkB oxidoreductase to prepare a mixture of oxidation products of an alkane, wherein the ratio of carboxylic acid to alcohol in the oxidation products is preferably greater than 1:1.

20 Claims, 11 Drawing Sheets

(56) References Cited

U.S. PATENT DOCUMENTS

| | | |
|---|---|---|
| 2010/0167360 A1 | 7/2010 | Thum et al. |
| 2010/0190224 A1 | 7/2010 | Poetter et al. |
| 2010/0248325 A1 | 9/2010 | Eckstein et al. |
| 2010/0261237 A1 | 10/2010 | Verseck et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0251399 A1 | 10/2011 | Dingerdissen et al. |
| 2012/0034665 A1 | 2/2012 | Haas et al. |
| 2012/0041216 A1 | 2/2012 | Sieber et al. |
| 2012/0264182 A1 | 10/2012 | Reinecke et al. |
| 2012/0315366 A1 | 12/2012 | Zehnacker et al. |
| 2013/0035403 A1 | 2/2013 | Schaffer et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0164797 A1 | 6/2013 | Gielen et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |
| 2013/0245276 A1 | 9/2013 | Klasovsky et al. |
| 2013/0331580 A1 | 12/2013 | Klasovsky et al. |
| 2014/0039071 A1 | 2/2014 | Thum et al. |
| 2014/0039210 A1 | 2/2014 | Erhardt et al. |
| 2014/0039223 A1 | 2/2014 | Klasovsky et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1 | 6/2014 | Schaffer et al. |
| 2014/0186905 A1 | 7/2014 | Schaffer et al. |
| 2014/0199736 A1 | 7/2014 | Köhler et al. |
| 2014/0242646 A1* | 8/2014 | Potter .............. C12P 13/001 435/128 |
| 2014/0256904 A1* | 9/2014 | Schaffer ............ C12N 9/0006 528/310 |
| 2014/0308717 A1* | 10/2014 | Haas ................. C12N 9/0006 435/126 |
| 2015/0010968 A1* | 1/2015 | Engel ................... C12P 7/04 435/136 |
| 2015/0099282 A1* | 4/2015 | Haas ................. C12N 9/0016 435/116 |
| 2015/0111253 A1* | 4/2015 | Schaffer ............. C07K 14/79 435/71.1 |
| 2015/0111254 A1* | 4/2015 | Hennemann .......... C12P 13/06 435/71.2 |
| 2015/0125912 A1* | 5/2015 | Haas ................... C12P 7/02 435/134 |
| 2015/0203629 A1* | 7/2015 | Ortelt ................. C08K 5/1535 428/418 |
| 2015/0209775 A1* | 7/2015 | Erhardt ................ B01J 39/04 564/388 |
| 2015/0218600 A1* | 8/2015 | Haas ................. C12N 9/0004 435/146 |
| 2015/0267231 A1* | 9/2015 | Haas ................. C12N 15/74 435/146 |
| 2015/0275245 A1* | 10/2015 | Haas ................. C12N 9/0077 435/158 |
| 2015/0284747 A1* | 10/2015 | Schiemann ........... C12P 7/16 435/141 |
| 2015/0299741 A1* | 10/2015 | Engel ................... C12P 7/18 435/158 |
| 2015/0307906 A1* | 10/2015 | Schaffer ............ C12N 9/0008 435/128 |
| 2015/0353963 A1* | 12/2015 | Haas ................ C12Y 114/1500 435/158 |

FOREIGN PATENT DOCUMENTS

| | | |
|---|---|---|
| WO | WO 2013/024114 A2 | 2/2013 |
| WO | WO 2013/092426 A1 | 6/2013 |
| WO | WO 2013/110557 A1 | 8/2013 |
| WO | WO 2013/156454 A1 | 10/2013 |

OTHER PUBLICATIONS

Van Beilen, J.B., et al., 1992, "Topology of the membrane-bound alkane hydroxylase of Pseudomonas oleovorans", Journal of Biological Chemistry, vol. 267, No. 13, pp. 9194-9201.*

Shanklin, J., et al., 1997, "Mossbauer studies of alkane omega-hydroxylase: evidence tor a diiron cluster in an integral membrane enzyme", Proceedings of the National Academy of Sciences, U.S.A., vol. 94, pp. 2981-2986.*

Lee, H.J., et al., 1998, "Electron transfer from flavin to iron in the Pseudomonas oleovorans rubredoxin reductaserubredoxin electron transfer complex", Biochemistry, vol. 37, No. 44, pp. 15513-15522.*

Canosa, I., et al., 2000, "A positive feedback mechanism controls expression of AlkS, the transcriptional regulator of the Pseudomonas oleovorans alkane degradation pathway", Molecular Microbiology, vol. 35, No. 4, pp. 791-799.*

Perry, A. et al., 2001, "Two-iron rubredoxin of Pseudomonas oleovorans: production, stability and characterization of the individual iron-binding domains by optical, CD and NMR spectra copies", Biochemical Journal, vol. 354, No. 1, pp. 89-98.*

Shanklin, J., et al., 2003, "Evidence linking the Pseudomonas oleovorans alkane ω-hydroxylase, an integral membrane diiron enzyme, and the fatty acid desaturase family", FEBS Letters, vol. 545, pp. 188-192.*

Marin, M.M., et al., 2003, "Differential expression of the components of the two alkane hydroxylases from Pseudomonas aeruginosa", Journal of Bacteriology, vol. 185, No. 10, pp. 3232-3237.*

Perry, A., et al., 2004, "Solution structure of the two-iron rubredoxin of Pseudomonas oleovorans determined by NMR spectroscopy and solution X-ray scattering and interactions with rubredoxin reductase", Biochemistry, vol. 43, No. 11, pp. 3167-3182.*

Chakrabarty, A.M., et al., 1973, "Genetic regulation of octane dissimilation plasmid in Pseudomonas", Proceedings of the National Academy of Sciences, U.S.A., vol. 70, No. 4, pp. 1137-1140.*

Van Beilen, J.B., et al., 1994, "Genetics of alkane oxidation by Pseudomonas oleovorans", Biodegradation, vol. 5, pp. 161-174.*

Grant, C., et al., 2011, "Whole-cell bio-oxidation of n-dodecane using the alkane hydroxylase system of P. putida GPo1 expressed in E. coli", Enzyme and Microbial Technology, vol. 48, Nos. 6-7, pp. 480-486.*

Patel, R.N., et al., 1983, "Oxidation of alkanes by organisms grown on C2—C4 alkanes", Journal of Applied Biochemistry, vol. 5, Nos. 1-2, pp. 107-120.* van Beilen et al., "Analysis of Pseudomonas putida alkane-degradation gene clusters and flanking insertion sequences: evolution and regulation of the alk genes", Microbiology 147: 1621-1630 (2001).*

International Search Report dated Dec. 21, 2012 in Patent Application No. PCT/EP2012/073334.

Chris Grant, et al., "Whole-cell bio-oxidation of n-dodecane using the alkane hydroxylase system of P. putida GPo1 expressed in E. coli" Enzyme and Microbial Technology, vol. 48, No. 6-7, XP 2667148A, May 2011, pp. 480-486.

Johnson, E. L., "Gasoline oxygenate biodegradation processes in Mycobacterium vaccae JOB5" Retrieved from the Internet: URL:http://search.proquest.com/docview/305395658?accountid=29404, Chapter 5: "Propane and n-Butane Oxidation by Pseudomonas putida GPo1", XP 8148917, 2005, 154 pages.

Jan B. van Beilen, et al., "Substrate specificity of the alkane hydroxylase system of Pseudomonas oleovorans GPo1" Enzyme and Microbial Technology, vol. 16, No. 10, XP 23679643A, 1994, pp. 904-911.

Tadashi Fuji, et al., "Biotransformation of Various Alkanes Using the Escherichia coli Expressing an Alkane Hydroxylase System

(56) References Cited

OTHER PUBLICATIONS from *Gordonia* sp. TF6", Bioscience, Biotechnology, and Biochemistry, vol. 68, No. 10, XP 2669751A, 2004, pp. 2171-2177.

Eva J. McKenna, et al., "Enzymatic omega-Oxidation IV. Purification and properties of the omega-hydroxylase of Pseudomonas oleovorans", Journal of Biological Chemistry, vol. 245, No. 15, XP 2671879A, 1970, pp. 3882-3889.

Marcel G. Wubbolts, et al., "Biosynthesis of Synthons in Two-Liquid-Phase Media" Biotechnology and Bioengineering, vol. 52, No. 2, XP 972414A, Oct. 1996, pp. 301-308.

Chris Grant, et al., "Tools for Characterizing the Whole-Cell Bio-Oxidation of Alkanes at Microscale" Biotechnology and Bioengineering, vol. 109, No. 9, XP 2688926A, Apr. 2012, pp. 2179-2189.

Patel et al.—"Oxidation of Alkanes by Organisms Grown on $C_2$—$C_4$ Alkanes", Journal of Applied Biochemistry 5, pp. 107-120 (1983).

Daniel J. Koch et al. "In Vivo Evolution of Butane Oxidation by Terminal Alkane Hydroxylases AlkB and CYP153A6", American Society for Microbiology, vol. 75, No. 2, Jan. 2009, pp. 337-344 (with cover page).

Erika L. Johnson et al. "Propane and n-Butane Oxidation by *Pseudomonas putida* GPo1", American Society for Microbiology, vol. 72, No. 1, Jan. 2006, pp. 950-952 (with cover page).

\* cited by examiner

SEQUENCE LISTING

```
<160> NUMBER OF SEQ ID NOS: 8

<210> SEQ ID NO 1
<211> LENGTH: 39
<212> TYPE: DNA
<213> ORGANISM: Artificial Sequence
<220> FEATURE:
<223> OTHER INFORMATION: Synthetic Primer

<400> SEQUENCE: 1
aaaaattgga gaattatgtc agagaacatt ttaaccgag                              39

<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
ctaatcttca tggaggacat agtc                                             24

<210> SEQ ID NO 3
<211> LENGTH: 39
<212> TYPE: DNA
<213> ORGANISM: Artificial Sequence
<220> FEATURE:
<223> OTHER INFORMATION: Synthetic Primer

<400> SEQUENCE: 3
ctccatgaag attagtcgac ctgtaacgac aacaaaacg                              39
```

<210> SEQ ID NO 4
<211> LENGTH: 39
<212> TYPE: DNA
<213> ORGANISM: Artificial Sequence
<220> FEATURE:
<223> OTHER INFORMATION: Synthetic Primer

<400> SEQUENCE: 4
cgttgcttcg caacgttaga aaacatatga cgcaccaag              39

<210> SEQ ID NO 5
<211> LENGTH: 11353
<212> TYPE: DNA
<213> ORGANISM: Artificial Sequence
<220> FEATURE:
<223> OTHER INFORMATION: Synthetic Vector

<400> SEQUENCE: 5

| | | | | | |
|---|---|---|---|---|---|
| gcccggaggg | tggcgggcag | gacgcccgcc | ataaactgcc | aggcatcaaa | ttaagcagaa | 60 |
| ggccatcctg | acggatggcc | ttttgcgtt | tctacaaact | cttttgttta | ttttttctaaa | 120 |
| tacattcaaa | tatgtatccg | ctcatgagac | aataaccctg | ataaatgctt | caataatgca | 180 |
| gcctgaaagg | caggccgggc | cgtggtggcc | acggcctcta | ggccagatcc | agcggcatct | 240 |
| gggttagtcg | agcgcgggcc | gcttcccatg | tctcaccagg | gcgagcctgt | ttcgcgatct | 300 |
| cagcatctga | atcttcccg | gccttgcgct | tcgctgggc | cttacccacc | gccttggcgg | 360 |
| gcttcttcgg | tccaaaactg | aacaacagat | gtgtgacctt | gcgcccggtc | tttcgctgcg | 420 |
| cccactccac | ctgtagcggg | ctgtgctcgt | tgatctgcgt | cacggctgga | tcaagcactc | 480 |
| gcaacttgaa | gtccttgatc | gagggatacc | ggccttccag | ttgaaaccac | tttcgcagct | 540 |
| ggtcaatttc | tatttcgcgc | tggccgatgc | tgtcccattg | catgagcagc | tcgtaaagcc | 600 |
| tgatcgcgtg | ggtgctgtcc | atcttggcca | cgtcagccaa | ggcgtatttg | gtgaactgtt | 660 |
| tggtgagttc | cgtcaggtac | ggcagcatgt | ctttggtgaa | cctgagttct | acacggccct | 720 |
| caccctcccg | gtagatgatt | gtttgcaccc | agccggtaat | catcacactc | ggtcttttcc | 780 |
| ccttgccatt | gggctcttgg | gttaaccgga | cttcccgccg | tttcaggcgc | agggccgctt | 840 |
| cttttgagctg | gttgtaggaa | gattcgatag | ggacacccgc | catcgtcgct | atgtcctccg | 900 |
| ccgtcactga | atacatcact | tcatcggtga | caggctcgct | cctcttcacc | tggctaatac | 960 |
| aggccagaac | gatccgctgt | tcctgaacac | tgaggcgata | cgcggcctcg | accagggcat | 1020 |
| tgcttttgta | aaccattggg | ggtgaggcca | cgttcgacat | tccttgtgta | taagggggaca | 1080 |
| ctgtatctgc | gtcccacaat | acaacaaatc | cgtcccttta | caacaacaaa | tccgtccctt | 1140 |
| cttaacaaca | aatccgtccc | ttaatggcaa | caaatccgtc | ccttttttaaa | ctctacaggc | 1200 |
| cacggattac | gtggcctgta | gacgtcctaa | aaggtttaaa | agggaaaagg | aagaaaaggg | 1260 |
| tggaaacgca | aaaaacgcac | cactacgtgg | ccccgttggg | gccgcatttg | tgcccctgaa | 1320 |
| ggggcggggg | aggcgtctgg | gcaatccccg | ttttaccagt | ccctatcgc | cgcctgagag | 1380 |
| ggcgcaggaa | gcgagtaatc | agggtatcga | ggcggattca | cccttggcgt | ccaaccagcg | 1440 |
| gcaccagcgg | cgcctgagag | gcgaattgac | ataagcctgt | tcggttcgta | aactgtaatg | 1500 |
| caagtagcgt | atgcgctcac | gcaactggtc | cagaaccttg | accgaacgca | gcggtggtaa | 1560 |
| cggcgcagtg | gcggttttca | tggcttgtta | tgactgtttt | tttgtacagt | ctatgcctcg | 1620 |
| ggcatccaat | cgatgggaag | ccctgcaaag | taaactggat | ggctttcttg | ccgccaagga | 1680 |
| tctgatggcg | cagggggatca | agatctgatc | aagagacagg | atgaggatcg | tttcgcatga | 1740 |

```
ttgaacaaga tggattgcac gcaggttctc cggccgcttg ggtggagagg ctattcggct    1800
atgactgggc acaacagaca atcggctgct ctgatgccgc cgtgttccgg ctgtcagcgc    1860
aggggcgccc ggttcttttt gtcaagaccg acctgtccgg tgccctgaat gaactgcagg    1920
acgaggcagc gcggctatcg tggctggcca cgacgggcgt tccttgcgca gctgtgctcg    1980
acgttgtcac tgaagcggga agggactggc tgctattggg cgaagtgccg gggcaggatc    2040
tcctgtcatc tcaccttgct cctgccgaga agtatccat catggctgat gcaatgcggc      2100
ggctgcatac gcttgatccg gctacctgcc cattcgacca ccaagcgaaa catcgcatcg    2160
agcgagcacg tactcggatg gaagccggtc ttgtcgatca ggatgatctg gacgaagagc    2220
atcaggggct cgcgccagcc gaactgttcg ccaggctcaa ggcgcgcatg cccgacggcg    2280
aggatctcgt cgtgacccat ggcgatgcct gcttgccgaa tatcatggtg aaaatggcc     2340 gcttttctgg attcatcgac tgtggccggc tgggtgtggc ggaccgctat caggacatag    2400
cgttggctac ccgtgatatt gctgaagagc ttggcggcga atgggctgac cgcttcctcg    2460
tgctttacgg tatcgccgct cccgattcgc agcgcatcgc cttctatcgc cttcttgacg    2520
agttcttctg agcgggactc tggggttcga aatgaccgac caatcgattg gtaactgtca    2580
gaccaagttt actcatatat actttagatt gatttaaaac ttcattttta atttaaaagg    2640
atctaggtga agatcctttt tgataatctc atgaccaaaa tcccttaacg tgagttttcg    2700
ttccactgag cgtcagaccc cgtagaaaag atcaaaggat cttcttgaga tcctttttt    2760 ctgcgcgtaa tctgctgctt gcaaacaaaa aaaccaccgc taccagcggt ggtttgtttg    2820
ccggatcaag agctaccaac tcttttccg aaggtaactg gcttcagcag agcgcagata    2880
ccaaatactg tccttctagt gtagccgtag ttaggccacc acttcaagaa ctctgtagca    2940
ccgcctacat acctcgctct gctaatcctg ttaccagtgg ctgctgccag tggcgataag    3000
tcgtgtctta ccgggttgga ctcaagacga tagttaccgg ataaggcgca gcggtcgggc    3060
tgaacggggg gttcgtgcac acagcccagc ttggagcgaa cgatctacac cgaactgaga    3120
tacctacagc gtgagctatg agaaagcgcc acgcttcccg aagggagaaa ggcggacagg    3180
tatccggtaa gcggcagagt cggaacagga gagcgcacga gggagcttcc aggggaaac    3240 gcctggtatc tttatagtcc tgtcgggttt cgccacctct gacttgagcg tcgatttttg    3300
tgatgctcgt cagggggggcg gagcctatgg aaaaacgcca gcaacgcggc ctttttacgg    3360
ttcctggcct tttgctggcc ttttgctcac atgttctttc ctgcgttatc ccctgattct    3420
gtggataacc gtattaccgc ctttgagtga gctgataccg ctcgccgcag ccgaacgacc    3480
gagcgcagcg agtcagtgag cgaggaagcg gaagagcgcc tgatgcggta ttttctcctt    3540
acgcatctgt gcggtatttc acaccgcata ggggatctcc aatcgtgcct ggcgcagcg     3600 acagccctcg gtcccccaga tagccattga tcttctctcg cctgtcccct cagttcagta    3660
atttcctgca tttgcctgtt ccagtcggt agatattcca caaaacagca gggaagcagc     3720
gcttttccgc tgcataaccc tgcttcgggg tcattatagc gattttttcg gtatatccat    3780
ccttttccgc acgatataca ggattttgcc aaagggttcg tgtagacttt ccttggtgta    3840
tccaacggcg tcagccgggc aggataggtg aagtaggccc acccgcgagc gggtgttcct    3900
tcttcactgt cccttattcg cacctggcgg tgctcaacgg gaatcctgct ctgcgaggct    3960
ggccggctac cgccggcgta acagatgagg gcaagcggat ggctgatgaa accaagccaa    4020
ccaggaaggg cagcccacct atcaaggtgt actgccttcc agacgaacga agagcgattg    4080
```

-continued

```
aggaaaaggc ggcggcggcc ggcatgagcc tgtcggccta cctgctggcc gtcggccagg      4140
gctacaaaat cacgggcgtc gtggactatg agctcgagaa cgcttaccgc caacacagca      4200
gtgtatttga ataagagctc gaacatgatc ggatctccca tttcagcaag ggaaatccca      4260
ccatagccac caccgattta tgtggcgtag aaaacggtca tcaccaaata tggcaatact      4320
tccccgccca agcgccacat aacagcctgg gccacatttt acgcggtagt tccgcacgta      4380
cggagtgcgg ggggcggcag gtaactgccg tccctatcgc gaccgttggt tcgagtggct      4440
gagcatcatt gctaatcagg taattttata ctccctgcaa gcgcaccttg acgtttaggc      4500
aaatttattg tctcagttgc aatcagtcgc tcctgcttgt acgcaaggac ttctagttca      4560
agagtttcgt tattaattgc aacaacgagt ttatcgtagt cctttagagc accaagtcct      4620
tgcagcgcca tcccttaag atcagaccag aaccgtggtg gggttggtgc tggtgttgat       4680
gtgccacaga tgctacttgc gacaatttga gcgtgtgtaa ccgcattatg aattgtctct      4740
aaacgtacca tcgttcccca aaaggatttt ctagccattg cgcagtcgcc gattgcatat      4800
atacttgtat ccgatgtaca catctgatca tcgaccacaa caccattact cacttcaagg      4860
gccgcctcag ttgccagctc tagctctggg atagcaccga ttccaactac aatcagatcc      4920
gcctgaattt cttctccact ttcaagtacg cattgttcaa catggccatt cctgcccttt      4980
atagacgtta atttcgcatt cagcttgaac tcaattcctt cagcctccag gcgggctctg      5040
actaagtttg ctgctgccgg cgtaaccacg cgcgccatta cacgcggggc ggcttctatc      5100
actgtgaccc tcttccctaa gccaccgca gctgaggcga cttcaagccc gattactccg       5160
ccgcccaaca caacaacaga cgcactctcc acaagtttcc tacgtaaatt tttggcgtct      5220
tccatactgc gtaaatagca gaccccagac agttcagacc cctcgcaggt taacctacgt      5280
gcgctagcac ctgttgcaag aatcaatttt tcatacgcgt attcttttcc atctttagaa      5340
gaaactatct tacgccccac gtcgattgat acaatcggtg tatttaacga aatggtaata      5400
ttgttattcg tataaaaacc ttctggcttt aatggcactg cggattctgc aatctcactt      5460
gtcagaaaag ccttggatag aggaggccgc tgataaggcg ccacagactc cctgctaaaa      5520
atcctaattt ccccttata accatattga cgaagccaga acgcagcatt tactccagct       5580
gtaccagcgc caacaacaac gattgccata attctctctc cggtatactt ttcactatat      5640
cacttaatgc cgattatttt agataattcc ttgacgctca gcttcaattg ttgcttgcgt      5700
gcgattcact acattcaagg tggcaaatat tttcctcata tgccacttta tagcatcttc      5760
ggtgacatgc atatttgttg ctatttgttt gtttgagcac ccctcttta caagcctcaa       5820 gacagcaatc tgcttccgtg tcaataaagc gtcagcttta ttctctgcgg actttccaat      5880
ctcaactatt cgcggaagac taaaagcccc aatcgcttga tctaaattaa ctgctgtgaa      5940
ggcttcacat gaagccggta ttattcgctc aattaaacat acttcatcaa gaactgtttg      6000
aaagcattga agctgttttg ctatctccac tgcataaaca atgttaagct gagccttttt      6060
taaatcaccg gcacctgcct gcgctccggc caaacacaat aatccacgga cttccagctg      6120
gcccgcgtta attttacggg cttgctgaat agccaataac gctctgtgcg cggcactatg      6180
aaagttccga tctcgggaaa gcactagtga ttgaacaagc agcaggcgtg cttttagggg      6240
ggctgagtgc tgtccggaga aaatcttatg atcttcaaga gttttttaaat tatttatgcc     6300 cgttatgcct tgacagacta agcgctgata gatctcaatt tggctcataa cttccaatct     6360
tggtagattt ttttcaaccg catgcgcctt cgccactcc aatatctcaa tggagccatt       6420
taggtcactc cttccaagcc gccaagctga cacagcacgg catacggaaa aaaacacgtc      6480
```

```
tgtcacccg tgattggaaa tgaactctaa aattttggag agcttttctt ctgaggtgtc    6540
caagcagcgc aattcataat gtaactcaag ctctagagcg tcaaacattt tcgaagtaaa    6600
ctcggattcc atcatctgcg cgcgactgtc tgtgcgtgct tgagttataa tctgcctcgc    6660
ccagcccatt tttccgcttg ctagggcttg ttgaaacctc gcgacataca gccaaccaaa    6720
agcaaaattt tgttttgcaa atttattcac ggcttgggcc tgagccagca ccttctccaa    6780
ctctgcaaat ctatactcac tggcaaaaat aaaagccaaa caggttagcg cggcccttt    6840 tccaactgcg tttgaatccc caaataaact aatccactta ttacagagct cctcactcga    6900
aagcatttca tctttcgttg ctttacctat tgcaagcaca agctgcagcc attccttttc    6960
ttgccattta tttttttat cggattgtga agataggtct ttaattaact tctctgctcg    7020
cgcgccttgc tgactgaaat acaatacca cgcgtaacta ataagcacta tgggtttttt    7080
gtgccaggcc tgcttcggca gctctaacag ccactgtctc agcgcatcta tttcgccctg    7140
acgaaatgac aaatctaaaa ttattctctc agacatgctg actgcccagc gacagtcatt    7200
cgcccgtagg gatattcgta ttgcatactg gtattcacct ctacgccaat gccagaaagc    7260
tgcacgctta agcaggtagg atcttttagc aggattttca gtccaagtaa tttctcgtag    7320
aaaattacgc agtactggat gcagtgtaaa ctgcgctggc tcaccgctca catggcgaag    7380
caacatgtaa ttagtgctta aatacttaat acatgagacc ccattgacgc atttgaatac    7440
ataattgtat tgatcaggcg tcacgaaatc gagcaatgaa gaatttgcaa gaaaaacacg    7500
atagcgctcg ggaatcgcct caaatatttc atccctaaag taattgtcta cttcaactac    7560
tgctgaaata tgcttggccg gcaactcacg ctttaacaaa aaaactacaa gagcaggcca    7620
cccctcaact tcttgcacca aggtctctat ctgttcttca ggaactccaa gaacagactc    7680
tgcctccgct aacgccaccg cctcttctgc gctaaaggcc aagtctttct cggtgtactc    7740
ccgcatagcg cctgcaagtt taagctgcga gaacccttt attgtattgc ctgcaactgc    7800
aaacctgata tttttggtg tatttaacat aaactccata agtgcgtgca acaacggcaa    7860
gtctaagtca tgattaatat tatccaaaca aactagcgtt tctatctcgt tattcgaggt    7920
gctctgccaa agactagatg caaggtctcg caagagcgca ggcttgctca caccctctct    7980
cacacggctg aattttacca tttcgaaagt ttcaagctgc tcaataatct ctgcgcagat    8040
atcaaattca ctgtaagaac tggctcttaa agaaagccac actgcaggac gtccggctgt    8100
tctgtggcgt agccactcga acgcaagagc aacggttttc ccatatccag gtggggctct    8160
gtaaaggcat actctgggag cggctccatc cgcgatactc aatcttggcc gatatatgca    8220
actatgaact ttggcactta ctagagtcgt aatttgatcc gctccgacct tagcgaccgg    8280
gaaatcatta tttattatta ttttcattat gctattctcg cgccagctga ctggaaattt    8340
tcaccatagg ttacggtgtt aaatattaaa actacactta agtgtagtcg gcatgatcgg    8400
tggtgcaaaa tatttactag ggaaggtctg aagtaggccg ctatttctgg ccgacttcgg    8460
ccttcgccga ttttgaagac gggcaccggg tcaaaatcga ccagatagct cgctcatttc    8520
ggtgctttca gccgtcgcga gtagctcgcg gtacctggca tgcttgcggc cagtcgtgt    8580 ttttccagca gacgacggag caaaaactac ccgtaggtgt agttggcgca agcgtccgat    8640
tagctcaggt ttaagatgtc gagagtgaga gtgggcggct taactttctc agttaggcat    8700
aaaattacgt cttaaatctc gtagcgacta atttaataaa aattggagaa ttatgtcaga    8760
gaacatttta accgagcccc cacgaagtga tgctgataat gagggttatg tggaccgaaa    8820
```

```
gcgccacttg tggattcttt ctgtactgtg ccagcaaca ccaataattg cctatatct    8880
cgtatcccaa acagggtgga gtatatggta cggattagta ttaatcctat ggtacggcct   8940
agtccctttg atcgacacca tgcttggcga ggattattcc aaccctcctg aatccgttgt   9000
tcctaagctt gaacaagacc gttactacaa agttttaacg tacttaaccg ttcctattca   9060
ttatgcagcg ttgattataa gtgcctggtg ggtatctacc caaccaatag gggtattcga   9120
gtttttagct ctcgcccttt ctttgggcat tgttaatgga ctggcactca acacaggcca   9180
tgaactcggg cataaaaaag aaacctttga ccgctggatg gccaagcttg tactggccgt   9240
ggtcggatat ggtcacttct tcattgaaca caataaaggg catcatcgtg acgtagcaac   9300
accgatggac ccggctacat cccgcatggg cgaatctatt tatacgtttt cactgcgtga   9360
aattcctggt gcctttaaac gggcatgggg cttggaagag cagcgcctca gccgttgcgg   9420
caaaagcgta tggagcctag ataatgaagt cttacagcct atgattttga cggtagtgct   9480
ttatgccgca ttgctggcat ttttcggtcc tttaatgctc atcttttgc ccattcaaat   9540
ggccttcggc tggtggcagc tgaccagtgc caattatatt gagcactacg gactgctgcg   9600
tgaaaagctg ccgaacgggc gttacgagca tcaaaaaccc catcattcat ggaattcaaa   9660
ccatgtaatg tcgaaccctca tcctgtttca tctgcaacgt cattcagatc accatgcgca   9720
tcctacaaga tcttatcaat cacttaggga cttcagcgac cttcccaccc tgcctacggg   9780
ctaccctggg atgttcttcg tcgcattctt tccctcctgg tttcgttcac taatggatga   9840
tcgggtgatg gagtgggcgc acggagacat taataagatc cagattcagc cgggaatgcg   9900
tgaattctat gagcaaaaat ttggagtaaa gggttcggag tcacccgata caaccgttgc   9960
caaataatcg ccaacagaaa tccatctatt aaagctcgtg ctttcacact tgaggaaca   10020
gcgcccggcg tgtacgtcgg gcgccattaa ctaaagacaa taatattggt tcaaaggtgc   10080
tttaaatggc taaatatcaa tgccccgatt gcgaatatat atacgatgaa gtcgctggcc   10140
acccacacga aggcttcccc ccaggaacgt cttgggaaac gattcctgaa gagtgggcct   10200
gcccagactg tgcagtaagg gataaagctg acttcgtagt aatagaatcc ggttccgcgt   10260
ccccggcgtc tggcgcggcc accccagaag tgcgcactgc taccacccca cctaaggcag   10320
aggcttcacc tcaaaaatca acgggggcct cgactccttc agctaacaat aaagccaaag   10380
caaaggctaa agccaaaccc gcacgggcaa atcgtctaa agactccacc ggcaaagaga   10440
ccacctttcg taaatggatc tgtatcactt gcggtcacat ttatgatgaa gctcttggcg   10500
atgaaactga agggttcgcg ccaggcactc ttttttgaaga tatcccggac gattggtgct   10560
gtcccgactg tggtgccaca aaagaggact atgtcctcca tgaagattag tcgacctgta   10620
acgacaacaa aacgagggta gcacaatgag ttttttctaat tataaagtaa tcgcgatgcc   10680
ggtgttggtt gctaattttg ttttgggggc ggccactgca tgggcgaatg aaaattatcc   10740
ggcgaaatct gctggctata atcagggtga ctgggtcgct agcttcaatt tttctaaggt   10800
ctatgtgggt gaggagcttg gcgatctaaa tgttggaggg ggggctttgc caaatgctga   10860
tgtaagtatt ggtaatgata caacacttac gtttgatatc gcctattttg ttagctcaaa   10920
tatagcggtg gatttttttg ttggggtgcc agctagggct aaatttcaag gtgagaaatc   10980
aatctcctcg ctgggaagag tcagtgaagt tgattacggc cctgcaattc tttcgcttca   11040
atatcattac gatagctttg agcgacttta tccatatgtt ggggttggtg ttggtcgggt   11100
gctattttt gataaaaccg acggtgcttt gagttcgttt gatattaagg ataaatgggc   11160
gcctgctttt caggttggcc ttagatatga ccttggtaac tcatggatgc taaattcaga   11220
```

```
tgtgcgttat attcctttca aaacggacgt cacaggtact cttggcccgg ttcctgtttc    11280
tactaaaatt gaggttgatc ctttcattct cagtcttggt gcgtcatatg ttttctaacg    11340
ttgcgaagca acg                                                       11353
```

<210> SEQ ID NO 6
<211> LENGTH: 401
<212> TYPE: PRT
<213> ORGANISM: Pseudomonas putida Gpo1
<220> FEATURE:
<221> NAME/KEY: MISC_FEATURE
<222> LOCATION: (1)..(401)
<223> OTHER INFORMATION: Databank Code: CAB54050.1AlkB

<400> SEQUENCE: 6

```
Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
            20                  25                  30

Met Ile Gly Ile Trp Leu Ala Asn Glu Thr Gly Trp Gly Ile Phe Tyr
        35                  40                  45

Gly Leu Val Leu Leu Val Trp Tyr Gly Ala Leu Pro Leu Leu Asp Ala
    50                  55                  60

Met Phe Gly Glu Asp Phe Asn Asn Pro Pro Glu Glu Val Val Pro Lys
65                  70                  75                  80

Leu Glu Lys Glu Arg Tyr Tyr Arg Val Leu Thr Tyr Leu Thr Val Pro
                85                  90                  95

Met His Tyr Ala Ala Leu Ile Val Ser Ala Trp Trp Val Gly Thr Gln
            100                 105                 110

Pro Met Ser Trp Leu Glu Ile Gly Ala Leu Ala Leu Ser Leu Gly Ile
        115                 120                 125

Val Asn Gly Leu Ala Leu Asn Thr Gly His Glu Leu Gly His Lys Lys
    130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
        195                 200                 205

Leu Glu Glu Gln Arg Leu Ser Arg Arg Gly Gln Ser Val Trp Ser Phe
    210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
        275                 280                 285

Gln Lys Pro His His Ser Trp Asn Ser Asn His Ile Val Ser Asn Leu
    290                 295                 300

Val Leu Phe His Leu Gln Arg His Ser Asp His His Ala His Pro Thr
305                 310                 315                 320
```

```
Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
            340                 345                 350

Arg Ser Val Met Asp Pro Lys Val Val Asp Trp Ala Gly Gly Asp Leu
        355                 360                 365

Asn Lys Ile Gln Ile Asp Asp Ser Met Arg Glu Thr Tyr Leu Lys Lys
    370                 375                 380

Phe Gly Thr Ser Ser Ala Gly His Ser Ser Thr Ser Ala Val Ala
385                 390                 395                 400

Ser

<210> SEQ ID NO 7
<211> LENGTH: 173
<212> TYPE: PRT
<213> ORGANISM: Pseudomonas putida Gpo1
<220> FEATURE:
<221> NAME/KEY: MISC_FEATURE
<222> LOCATION: (1)..(173)
<223> OTHER INFORMATION: Databank Code: CAB54052.1AlkG

<400> SEQUENCE: 7

Met Ala Ser Tyr Lys Cys Pro Asp Cys Asn Tyr Val Tyr Asp Glu Ser
1               5                   10                  15

Ala Gly Asn Val His Glu Gly Phe Ser Pro Gly Thr Pro Trp His Leu
            20                  25                  30

Ile Pro Glu Asp Trp Cys Cys Pro Asp Cys Ala Val Arg Asp Lys Leu
        35                  40                  45

Asp Phe Met Leu Ile Glu Ser Gly Val Gly Glu Lys Gly Val Thr Ser
    50                  55                  60

Thr His Thr Ser Pro Asn Leu Ser Glu Val Ser Gly Thr Ser Leu Thr
65                  70                  75                  80

Ala Glu Ala Val Val Ala Pro Thr Ser Leu Gly Lys Leu Pro Ser Ala
                85                  90                  95

Asp Val Lys Gly Gln Asp Leu Tyr Lys Thr Gln Pro Pro Arg Ser Asp
            100                 105                 110

Ala Gln Gly Gly Lys Ala Tyr Leu Lys Trp Ile Cys Ile Thr Cys Gly
        115                 120                 125

His Ile Tyr Asp Glu Ala Leu Gly Asp Glu Ala Glu Gly Phe Thr Pro
    130                 135                 140

Gly Thr Arg Phe Glu Asp Ile Pro Asp Asp Trp Cys Cys Pro Asp Cys
145                 150                 155                 160

Gly Ala Thr Lys Glu Asp Tyr Val Leu Tyr Glu Glu Lys
                165                 170

<210> SEQ ID NO 8
<211> LENGTH: 385
<212> TYPE: PRT
<213> ORGANISM: Pseudomonas putida Gpo1

<400> SEQUENCE: 8

Met Ala Ile Val Val Val Gly Ala Gly Thr Ala Gly Val Asn Ala Ala
1               5                   10                  15

Phe Trp Leu Arg Gln Tyr Gly Tyr Lys Gly Glu Ile Arg Ile Phe Ser
            20                  25                  30

Arg Glu Ser Val Ala Pro Tyr Gln Arg Pro Pro Leu Ser Lys Ala Phe
        35                  40                  45
```

```
Leu Thr Ser Glu Ile Ala Glu Ser Ala Val Pro Leu Lys Pro Glu Gly
    50              55              60

Phe Tyr Thr Asn Asn Ile Thr Ile Ser Leu Asn Thr Pro Ile Val
65              70              75              80

Ser Ile Asp Val Gly Arg Lys Ile Val Ser Ser Lys Asp Gly Lys Glu
            85              90              95

Tyr Ala Tyr Glu Lys Leu Ile Leu Ala Thr Pro Ala Ser Ala Arg Arg
            100             105             110

Leu Thr Cys Glu Gly Ser Glu Leu Ser Gly Val Cys Tyr Leu Arg Ser
            115             120             125

Met Glu Asp Ala Lys Asn Leu Arg Arg Lys Leu Val Glu Ser Ala Ser
    130             135             140

Val Val Val Leu Gly Gly Val Ile Gly Leu Glu Val Ala Ser Ala
145             150             155             160

Ala Val Gly Leu Gly Lys Arg Val Thr Val Ile Glu Ala Thr Pro Arg
            165             170             175

Val Met Ala Arg Val Val Thr Pro Ala Ala Ala Asn Leu Val Arg Ala
            180             185             190

Arg Leu Glu Ala Glu Gly Ile Glu Phe Lys Leu Asn Ala Lys Leu Thr
        195             200             205

Ser Ile Lys Gly Arg Asn Gly His Val Glu Gln Cys Val Leu Glu Ser
    210             215             220

Gly Glu Glu Ile Gln Ala Asp Leu Ile Val Val Gly Ile Gly Ala Ile
225             230             235             240

Pro Glu Leu Glu Leu Ala Thr Glu Ala Ala Leu Glu Val Ser Asn Gly
            245             250             255

Val Val Val Asp Asp Gln Met Cys Thr Ser Asp Thr Ser Ile Tyr Ala
            260             265             270

Ile Gly Asp Cys Ala Met Ala Arg Asn Pro Phe Trp Gly Thr Met Val
        275             280             285

Arg Leu Glu Thr Ile His Asn Ala Val Thr His Ala Gln Ile Val Ala
    290             295             300

Ser Ser Ile Cys Gly Thr Ser Thr Pro Ala Pro Thr Pro Pro Arg Phe
305             310             315             320

Trp Ser Asp Leu Lys Gly Met Ala Leu Gln Gly Leu Gly Ala Leu Lys
            325             330             335

Asp Tyr Asp Lys Leu Val Val Ala Ile Asn Asn Glu Thr Leu Glu Leu
            340             345             350

Glu Val Leu Ala Tyr Lys Gln Glu Arg Leu Ile Ala Thr Glu Thr Ile
        355             360             365

Asn Leu Pro Lys Arg Gln Gly Ala Leu Ala Gly Ser Ile Lys Leu Pro
    370             375             380

Asp
385
```

BIOLOGICAL ALKANE OXIDATION

The invention relates to a method for oxidizing an alkane, comprising contacting the alkane with a type alkB oxidoreductase and using a type alkB oxidoreductase to prepare a mixture of oxidation products of an alkane, wherein the ratio of carboxylic acid to alcohol in the oxidation products is preferably greater than 1:1.

Alkanes represent some of the most important base materials in the chemical industry. Fossil raw materials are often a starting point for their production, meanwhile, however, methods for obtaining alkanes from renewable raw materials are also known. While alkanes are known to the public, particularly due to their usefulness as energy sources, for example, short-chain alkanes in the form of gases or liquid longer-chain alkanes, they are indispensable in the industry especially in their role as reactants or solvents for numerous syntheses which give rise to important products in daily life such as plastics or pharmaceuticals.

A fundamental condition for the use of alkanes for such purposes is the potential for the oxidative introduction of heteroatom-containing functions into the alkane carbon chains, e.g. hydroxyl, keto and carboxy functions, since alkanes per se can be characterized as relatively inert due to their chemical saturation. This must not, however, lead to a complete oxidation of alkanes to carbon dioxide, except when using alkanes as fuel, rather the heteroatom-containing functions must be introduced selectively and in a controlled manner.

Numerous reactions are known for the synthetic preparation of alkanes substituted with heteroatom-containing functions, for example, the halogenation of alkanes under the influence of UV light, the products of which can serve as reactants for the synthesis of numerous compounds. For instance, alcohols may be obtained by nucleophilic substitution of the halogen-substituted alkane. Such reactions, however, frequently require the use of toxic and/or environmentally harmful substances, chlorine gas for example, which is frequently used for halogenation due to its low industrial price.

A series of biotechnological methods for introducing heteroatom-containing, particularly oxygen-containing, functions into alkanes are also known. For instance, the conversion of propane to acetone by *Arthrobacter petroleophagus* and other wild-type strains is described in a patent by Exxon (EP 98137). Grant et al. (2011) use recombinant *E. coli* cells to oxidize long-chain alkanes.

Against this background, the object of the present invention is to develop a biotechnological method for oxidizing alkanes which is suitable for selective oxidation of a terminal carbon atom of an alkane up to the carboxylic acid.

Furthermore, it is an object of the present invention to develop a method which is suitable for preparing various products of the alkane oxidized selectively at the terminal carbon atom, wherein the amount and the ratio of the products can be influenced.

Furthermore, it is an object of the present invention to provide an oxidoreductase system which is able to catalyze the oxidation of a terminal carbon atom to all oxidation levels from the group comprising alcohol, aldehyde and carboxylic acid, wherein only a single catalytically active polypeptide comes into contact with the substrate alkane or intermediates thereof.

Furthermore, it is an object of the present invention to provide a characterized system for the selective terminal oxidation of alkanes, independent of fatty acid metabolism and by overexpression of an individual oxidation system.

A further object of the invention is to provide a method for oxidizing alkanes, preferably of gaseous alkanes, which is suitable for oxidizing the alkane predominantly or with improved yield to the carboxylic acid, not only predominantly to the alcohol.

These and other objects are achieved by the subject matter of the present application and particularly also by the subject matter of the accompanying independent claims, with embodiments arising from the dependent claims.

In a first aspect, the object of the invention is achieved by a method for oxidizing an alkane comprising contacting the alkane with a type alkB oxidoreductase in the presence of oxygen.

In a first embodiment of the first aspect, the alkane is an alkane having 1 to 5 carbon atoms.

In a second embodiment of the first aspect, which is also an embodiment of the first embodiment of the first aspect, the alkane is an alkane having 1 to 4 carbon atoms, preferably butane.

In a third embodiment of the first aspect, which is also an embodiment of the first and second embodiment of the first aspect, the alkane is a branched alkane, preferably having four or five carbon atoms, more preferably isobutane.

In a fourth embodiment of the first aspect, which is an embodiment of the first to third embodiment of the first aspect, the type alkB oxidoreductase is alkB from *Pseudomonas putida* GPO1 or a variant thereof.

In a fifth embodiment of the first aspect, which is also an embodiment of the first to fourth embodiment of the first aspect, the type alkB oxidoreductase is provided in the form of a whole-cell catalyst.

In a sixth embodiment of the first aspect, which is also an embodiment of the first to fifth embodiment of the first aspect, the type alkB oxidoreductase is provided in the form of a purified polypeptide.

In a second aspect, the object of the invention is achieved by using a type alkB oxidoreductase in the presence of oxygen for preparing a mixture of oxidation products of an alkane, wherein the ratio of carboxylic acid to alcohol in the oxidation products is preferably greater than 1:1.

In a first embodiment of the second aspect, the alkane is an alkane having 1 to 5 carbon atoms.

In a second embodiment of the second aspect, which is also an embodiment of the first embodiment of the second aspect, the alkane is an alkane having 1 to 4 carbon atoms, preferably butane.

In a third embodiment of the second aspect, which is also an embodiment of the first and second embodiment of the second aspect, the alkane is a branched alkane, preferably having four or five carbon atoms, more preferably isobutane.

In a fourth embodiment of the second aspect, which is also an embodiment of the first to third embodiment of the second aspect, the type alkB oxidoreductase is alkB from *Pseudomonas putida* GPO1 or a variant thereof.

In a fifth embodiment of the second aspect, which is also an embodiment of the first to fourth embodiment of the second aspect, the type alkB oxidoreductase is provided in the form of a whole-cell catalyst.

In a sixth embodiment of the second aspect, which is also an embodiment of the first to fourth embodiment of the second aspect, the type alkB oxidoreductase is provided in the form of a purified polypeptide.

In a seventh embodiment of the second aspect, which is also an embodiment of the first to sixth embodiment of the second aspect, the ratio of carboxylic acid to alcohol in the oxidation products is greater than 5:1, preferably greater than 12:1, more preferably greater than 20:1, most preferably greater than 40:1.

The inventors of the present invention have established that type alkB oxidoreductases, which are known in the literature as catalysts for preparing predominantly less strongly oxidized products, may be used, surprisingly, to prepare products predominantly of a higher oxidation level from alkanes, particularly from gaseous alkanes, particularly to give carboxylic acids starting from alkanes. In particular, the ratio of carboxylic acids produced to alcohols produced is surprisingly high. Furthermore, the inventors have found, surprisingly, that such oxidoreductases are capable of selective oxidation of alkanes, and produce by-products to be expected, particularly alkanes oxidized on carbon atoms other than terminal carbon atoms, only to an unexpectedly low extent or in amounts that are not detectable at all.

In accordance with the invention, alkanes, preferably gaseous alkanes, are oxidized using a type alkB oxidoreductase in the presence of oxygen. alkB represents an oxidoreductase which initially became known from the alkBGT system of *Pseudomonas putida* Gpo1, which is dependent on two further polypeptides, AlkG and AlkT. AlkT is characterized as a FAD-dependent rubredoxin reductase, which transfers the electrons from NADH to AlkG. AlkG is a rubredoxin, an iron-containing redox protein which functions as a direct electron donor to alkB. In a preferred embodiment, the same term "type alkB oxidoreductase" is a polypeptide having a sequence homology with increasing preference of at least 75, 80, 85, 90, 92, 94, 96, 98 or 99% of the sequence of the alkB of *Pseudomonas putida* Gpo1 (Databank code: CAB54050.1; this databank code originates like all others from the prior art used in the application, namely from the NCBI databank, more precisely the release available online on 15 Nov. 2011) having the capability to oxidize alkanes. In a particularly preferred embodiment, the type alkB oxidoreductase is a functionally interacting, alkane-oxidizing oxidoreductase having the AlkG (CAB54052.1) and AlkT (CAB54063.1) polypeptides from *Pseudomonas putida* Gpo1. In a most preferred embodiment, the type alkB oxidoreductase is alkB from the alkBGT system of *Pseudomonas putida* Gpo1 or a variant thereof.

The teaching of the present invention can be implemented not only by using the exact amino acid or nucleic acid sequences of the biological macromolecules described herein, but also by using variants of such macromolecules, which may be obtained by deletion, addition or substitution of one, or more than one, amino acids or nucleic acids. In a preferred embodiment, the term "variant" of a nucleic acid sequence or amino acid sequence, hereinafter used synonymously and interchangeably with the term "homologue", as used here, means another nucleic acid sequence or amino acid sequence, which has a homology, here used synonymously with identity, of 70, 75, 80, 85, 90, 92, 94, 96, 98, 99% or more percent, with respect to the corresponding original wild-type nucleic acid or amino acid sequence, wherein preferably the amino acids other than the amino acids forming the catalytically active centre or essential for the structure or folding are deleted or substituted or the latter are merely conservatively substituted, for example, a glutamate in place of an aspartate or a leucine in place of a valine. It is not necessary that the sequence has a correspondingly high homology over its entire length; fusion proteins or nucleic acids coding therefor may also be used in accordance with the invention which have a partial corresponding homology and/or activity. The prior art describes algorithms, which may be used to calculate the degree of homology of two sequences, e.g. Arthur Lesk (2008), Introduction to Bioinformatics, $3^{rd}$ edition. In a further more preferred embodiment of the present invention, the variant of an amino acid or nucleic acid sequence, preferably in addition to the sequence homologies mentioned above, has essentially the same enzymatic activity of the wild-type molecule and of the original molecule. For example, a variant of an enzymatically active polypeptide protease has the same, or essentially the same, proteolytic activity as the polypeptide enzyme, i.e. the capability to catalyze the hydrolysis of a peptide bond. In a particular embodiment, the term "essentially the same enzymatic activity" means an activity, with respect to the substrates of the wild-type polypeptide, which clearly lies above the background activity or/and differs from the $K_M$ and/or $k_{cat}$ values by less than 3, preferably 2, more preferably one order of magnitude, which the wild-type polypeptide exhibits with respect to the same substrates. In a further preferred embodiment, the term "variant" of a nucleic acid or amino acid sequence includes at least one active part/or fragment of the nucleic acid or amino acid sequence. In a further preferred embodiment, the term "active part", as used here, means an amino acid sequence or a nucleic acid sequence which has less than the full length of the amino acid sequence and/or codes for less than the full length of the amino acid sequence, wherein the amino acid sequence or the coded amino acid sequence with a shorter length than the wild-type amino acid sequence essentially has the same enzymatic activity as the wild-type polypeptide or a variant thereof, for example, alcohol dehydrogenase, monooxygenase or transaminase. In a particular embodiment, the term "variant" of a nucleic acid comprises a nucleic acid whose complementary strand, preferably under stringent conditions, binds to the wild-type nucleic acid. The stringency of the hybridization reaction is readily determinable by those skilled in the art and depends in general on the length of the probe, the washing temperatures and the salt concentration. Generally, longer probes require higher temperatures for the hybridization, whereas shorter probes work at lower temperatures. Whether hybridization takes place depends in general on the capability of the denatured DNA to anneal to complemetary strands which are present in its environment and below the melting temperature. The stringency of hybridization reactions and the corresponding conditions are described in more detail in Ausubel et al. (1995). In a preferred embodiment, the term "variant" of a nucleic acid, as used here, comprises any nucleic acid sequence which codes for the same amino acid sequence as the original nucleic acid or a variant of this amino acid sequence in terms of the degeneracy of the genetic code.

For many applications, the type alkB oxidoreductase used as part of a whole-cell catalyst is becoming the embodiment of choice, since it does not require any, or at least does not require full, purification of the oxidoreductase or its activity. In a preferred embodiment, the term "whole-cell catalyst", as used here, is understood to mean a metabolically active cell having an enzymatic activity of interest, preferably a type alkB oxidoredutase, preferably to an elevated degree relative to its wild-type, which can advantageously be attained by overexpression of a recombinant type alkB oxidoreductase on a plasmid or integrated into the genome. Numerous systems for preparing whole-cell catalysts are known to a person skilled in the art, for example, from DE 60216245. In a preferred embodiment, the cell used as whole-cell catalyst or as expression system is a prokaryotic, preferably a bacterial, cell. In a further preferred embodiment, said cell is a mammalian cell. In a further preferred embodiment, it is a lower eukaryotic cell, preferably a yeast cell. Examples of prokaryotic cells include *Escherichia*, particularly *Escherichia coli*, and strains of the genus *Pseudomonas* and *Corynebacterium*. Examples of lower eukaryotic cells include the genera *Saccharomyces, Candida, Pichia, Yarrowia, Schizosaccharomyces*, particularly the strains *Candida tropicalis, Schizosaccharomyces pombe, Pichia pastoris, Yarrowia lipolytica* and *Saccharomyces cerivisiae*. The cell may comprise one, or more than one, nucleic acid sequence on a plasmid or integrated into its genome coding for an enzyme used according to the invention. Methods for preparing such plasmids or cells may be routinely carried out by those skilled in the art. These methods are described in textbooks and experimental protocol collections of molecular biology, biochemistry, genetics and microbiology, for example, in Sambrook et al. (1989).

In a further preferred embodiment, the type alkB oxidoreductase is, however, a purified enzyme. In this case, all enzymatically active polypeptides used according to the invention may be cells comprising enzymatically active polypeptides or lysates thereof or preparations of the polypeptides in all stages of purification, from crude lysates up to the pure polypeptide. In a preferred embodiment, the term "purified" enzyme, as used here, is understood to mean in a preferred embodiment, that the whole cell, or an unprocessed extract thereof, is not used for the catalysis, rather the enzyme is partially or completely purified. In a particularly preferred embodiment, the term "purified" enzyme, as used here, means that the enzyme is purified in so far as it has, on an SDS gel of the preparation, with increasing preference, at least ca. 80, 85, 95, 98 or preferably 99% of the visible proteins. In a more preferred embodiment, the enzyme is purified in so far as it is the only recognizable polypeptide on an SDS gel of the corresponding preparation. Numerous methods are known to those experts in the field, by which enzymatically active polypeptides may be overexpressed in suitable cells and may be purified or isolated. Accordingly, all expression systems available to those skilled in the art for the expression of polypeptides may be used, for example, type pET or pGEX vectors. Chromatographic methods are suitable for purification, for example, the purification by affinity chromatography of a recombinant protein provided with a tag by using an immobilized ligand, for example, a nickel ion in the case of a histidine tag, immobilized glutathione in the case of a glutathione S-transferase fused to the target protein or immobilized maltose in the case of a tag comprising maltose-binding protein.

The purified enzymatically active polypeptide can either be used in soluble form or immobilized. Suitable methods are known to a person skilled in the art with which polypeptides may be covalently or non-covalently immobilized on organic or inorganic solid phases, for example, by sulphydryl coupling chemistry (e.g. kits from Pierce).

The teaching according to the invention may be applied to a multiplicity of alkanes. In a preferred embodiment, the term "alkane", as used here, is a saturated hydrocarbon from the group comprising linear and branched hydrocarbons of the empirical formula $C_nH_{2n+2}$ and cyclic hydrocarbons of the empirical formula $C_nH_{2n}$, where n may have the values 1, 2, 3, 4, 5, 6, 7, 8, 9, 10, 11, 12, 13, 14, 15, 16, 17, 18, 19, 20 and more, preferably 1 to 5, more preferably 1 to 4. Alkanes having 1 to 4 carbon atoms comprise, for example, the compounds methane, ethane, propane, butane and isobutane. The alkanes comprise linear alkanes, e.g. the group comprising methane, ethane, propane and butane. In a preferred embodiment, the alkane is a branched alkane, preferably from the group comprising isobutane, 2-methylbutane and neopentane. In a further particularly preferred embodiment, the alkane is an alkane from the group comprising butane and isobutane. In a further particularly preferred embodiment, said alkane is methylcyclobutane.

To perform the method according to the invention, various conditions are suitable. The presence of molecular oxygen as oxidizing agent is essential. The oxygen may be present in the form of oxygen sources such as hydrogen peroxide or potassium permanganate and be formed from these in situ, but particularly preferred is the introduction of oxygen gas, more preferably in the form of air, into the liquid reaction medium comprising the oxidoreductase. The temperature in this case may be more than 20° C., 30° C., 40° C., 50° C., 60° C., 70° C. or more than 80° C., preferably to 100° C., with the proviso that, in the case of the use of a living cell or of a suitable enzyme preparation, the chosen cell or the chosen enzymes are viable or show activity respectively. It is known to a person skilled in the art which organisms at which temperatures are viable, for example, from textbooks such as Fuchs/Schlegel, 2007. In the case of a living yeast cell, the temperature may be 5 to 45° C., preferably 15 to 42° C., more preferably 20 to 30° C. In the case of a gram-negative bacterium, preferably a bacterium from the family of the Enterobacteriaceae, most preferably *E. coli*, the temperature may be 5 to 45° C., preferably 15 to 42° C., more preferably 20 to 30° C., most preferably 35 to 40° C. The pH must be such that the activity of the type alkB oxidoreductase is at least maintained for an adequate length of time. In the case of the use of a whole-cell catalyst, the cell must remain intact for an adequate length of time. For example, the pH may be between 3 and 12, preferably 5 and 9, more preferably 6 and 8.

The alkane is preferably contacted with the type alkB oxidoreductase in such a way that the type alkB oxidoreductase, present in purified form or in the form of a whole-cell catalyst, is present in aqueous solution in a sufficiently stable form and the alkane is added to the solution with gentle stirring, together with oxygen, in the case of a solid or liquid alkane, or it is introduced into the aqueous solution in the form of a gas, if it is a gaseous alkane. The person skilled in the art has the ability to provide stabilized forms of the enzyme or whole-cell catalyst in the context of routine experiments. Factors to be observed, such as the use of a suitable buffer system, the setting of suitable values for temperature, pH and salt concentrations, are described in the literature, for example, in Cornish-Bowden, 1995.

For culturing the cells according to the invention, numerous culture media are possible, which may be supplemented with amino acids, for example, with 0.01 g/l tryptophan, or with glucose, for example, at a concentration of 1% (w/v), in the case of the use of a yeast cell, for example, YPD, YPN and YNB. In the case of the use of a bacterium from the family of the Enterobacteriaceae, preferably *E. coli*, culturing is possible in complete media such as LB medium or high cell density medium (HCD medium) consisting of $NH_4SO_4$ 1.76 g, $K_2HPO_4$ 19.08 g, $KH_2PO_4$ 12.5 g, yeast extract 6.66 g, $Na_3$ citrate 1.96 g, $NH_4Fe$ citrate (1%) 17 ml, trace element solution US3 5 ml, feeding solution (glucose 50% w/v, $MgSO_4 \times 7\ H_2O$ 0.5% w/v, $NH_4Cl$ 2.2% w/v) 30 ml per liter.

In a preferred embodiment, the cells used in the method according to the invention are cultured in another medium than the one used for the alkane oxidation. In a particularly preferred embodiment, the medium used for culturing is a complete medium and the medium used for alkane oxidation is a minimal medium. The method according to the invention, if carried out using viable cells, is carried out after culturing the cells preferably in transformation buffer containing, per liter, (NH$_4$)H$_2$PO$_4$ 8 g, NaCl 0.5 g, MgSO$_4$×7 H$_2$O 0.48 g, trace element solution US3 15 ml. 1 liter of trace element solution US3 is composed of HCl 37% 36.5 g, MnCl$_2$×4H$_2$O 1.91 g, ZnSO$_4$×7H$_2$O 1.87 g, Na-EDTA× 2H$_2$O 0.8 g, H$_3$BO$_3$ 0.3 g, Na$_2$MoO$_4$×2H$_2$O 0.25 g, CaCl$_2$× 2H$_2$O 4.7 g, FeSO$_4$×7 H$_2$O 17.8 g, CuCl$_2$×2H$_2$O 0.15 g and the pH of which is adjusted to 5.4. In a further embodiment, the alkane oxidation is carried out in M9 medium (15 g glucose, 6.79 g Na$_2$PO$_4$, 3 g KH$_2$PO$_4$, 0.5 g NaCl, 2 g NH$_4$Cl, 15 g yeast extract, 0.49 g MgSO$_4$*7H$_2$O, 1 ml TE and inoculated with 50 µg kanamycin in 1000 ml shaking flasks, where the trace element solution (TE) is composed per liter as follows: 36.5 g HCl 37%, 1.91 g MnCl$_2$*4H$_2$O, 1.87 g ZnSO$_4$*7H$_2$O, 0.84 g Na-EDTA*2H$_2$O, 0.3 g H$_3$BO$_3$, 0.25 g Na$_2$MoO$_4$*2H$_2$O, 4.7 g CaCl$_2$*2H$_2$O, 17.3 g FeSO$_4$*7H$_2$O and 0.15 g CuCl$_2$*2H$_2$O).

The method according to the invention may be carried out at atmospheric pressure. In the case of the use of gaseous alkane reactants, it may be advantageous, however, to allow the type alkB oxidoreductase to catalyse the reaction at higher pressures in the presence of a gas mixture, predominantly comprising a mixture of alkanes and oxygen, with increasing preference of more than 50, 60, 70 or 80 percent by volume. In a preferred embodiment, the pressure is more than 1.5, 2, 3 or 4 bar. In a further embodiment, the pressure is 0.5 to 4, preferably 1 to 3, most preferably 1 to 1.5 bar.

A particular advantage of the method according to the invention consists in that specific ratios of the oxidation products of the alkane used as reactant may be obtained. The alkane may, in principle, be oxidized to three oxidation levels, namely the alcohol, the aldehyde and the carboxylic acid, by the type alkB oxidoreductase on a terminal carbon atom, i.e. a carbon atom which is directly covalently bonded only to one further carbon atom at most. In a preferred embodiment, the statement that "the ratio of carboxylic acid to alcohol in the oxidation products is preferably greater than 1:1" means that the quantitative ratio of carboxylic acid to alcohol, preferably the quantitative ratio of carboxylic acid formed by oxidation of a terminal carbon atom to alcohol formed by oxidation of a terminal carbon atom is greater than 1:1, i.e. more molecules of the carboxylic acid formed by oxidation of a terminal carbon atom are present in the product mixture than molecules of the alcohol formed by oxidation of a terminal carbon atom.

In a preferred embodiment, a type alkB oxidoreductase, preferably alkB from *Pseudomonas putida* Gpo1, may be used to prepare oxidation products in the presence of oxygen from an alkane, preferably one having 1 to 5, more preferably 1 to 4 carbon atoms, most preferably 4 carbon atoms, wherein the ratio of carboxylic acid to alcohol is preferably greater than 1:1, with increasing preference 1.5:1, 2:1, 5:1, 10:1, 15:1 or 20:1.

In a further preferred embodiment, the invention comprises a method for the oxidation of a terminal carbon atom of a non-cyclic alkane to a corresponding aldehyde and/or a corresponding terminal monocarboxylic acid, comprising contacting the alkane with a biological agent, which comprises a catalytically active oxidoreductase, in the presence of an oxidizing agent, wherein the alkane is butane or isobutane and wherein the oxidoreductase is a type alkB oxidoreductase, more preferably the alkB monooxygenase from *P. putida* GPO1 or a homologue thereof and the oxidizing agent is oxygen and the use of a type alkB oxidoreductase, preferably the alkB monooxygenase from *P. putida* GPO1 or a homologue thereof for the oxidation of a terminal carbon atom of a non-cyclic alkane to a corresponding aldehyde and/or a corresponding terminal monocarboxylic acid, wherein the alkane is butane or isobutane.

The present invention is further illustrated by the following Figures and non-limiting examples, from which further features, embodiments, aspects and advantages of the present invention may be taken.

FIGS. 1a), b), c) and d) show the concentration of 1-butanol (a)), 2-butanol (b)), butyraldehyde (c)) and butyric acid (d)) as a time course during conversion of butane with oxygen by means of the alkBGT monooxygenase system of *P. putida* GPO1 at a stirring speed of 500-800 or 900 rpm. The concentrations in the fermenter (F) and in the wash bottle (WB) are shown.

FIGS. 2 a) and b) show the influence of the biomass concentration on the oxidation of butane by *E. coli* by the alkBGT monooxygenase system of *P. putida* GPO1, more precisely the concentration time course of 1-butanol (a)) and butyric acid (b)).

FIGS. 3a), b), c) and d) show the influence of the concentration of trace element (TE) solution on the oxidation of butane by *E. coli* by the alkBGT monooxygenase system of *P. putida* GPO1, more precisely the concentration time course of 1-butanol (a)), 2-butanol (b)), butyraldehyde (c)) and butyric acid (d)).

FIGS. 4a), b), c) and d) show a comparison of the strains *E. coli* BL21 and *E. coli* W3110 by the alkBGT monooxygenase system of *P. putida* GPO1 and the influence thereof on the oxidation of butane by *E. coli* with the monooxygenase (alkBGT) of *P. putida* GPO1, more precisely the concentration time course of 1-butanol (a)), 2-butanol (b)), butyraldehyde (c)) and butyric acid (d)).

FIGS. 5a), b), c) show the oxidation of isobutane by *E. coli* by the alkBGT monooxygenase system of *P. putida* GPO1, more precisely the concentration time course of 2-methyl-1-propanol (a)), isobutyraldehyde (b)) and isobutyric acid (c)).

Figure 1:
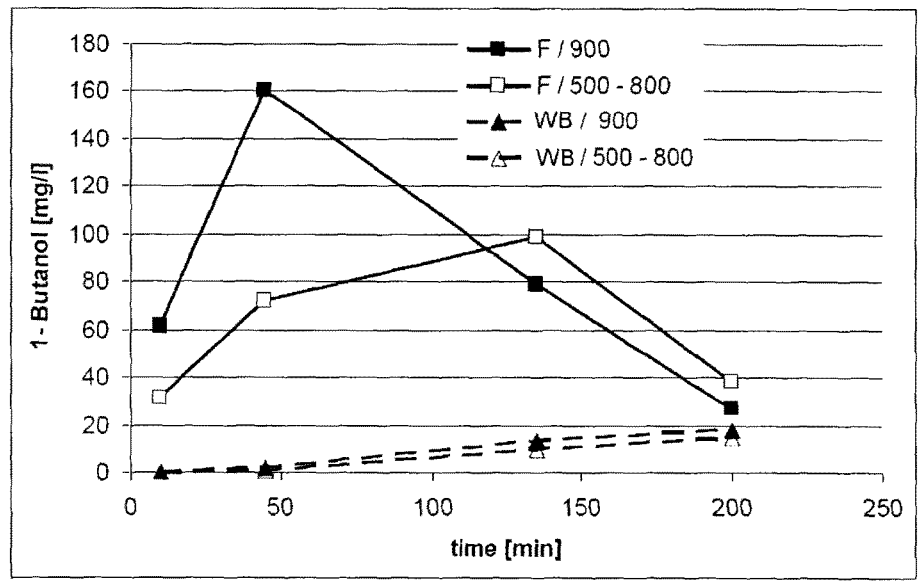
Figure 1:
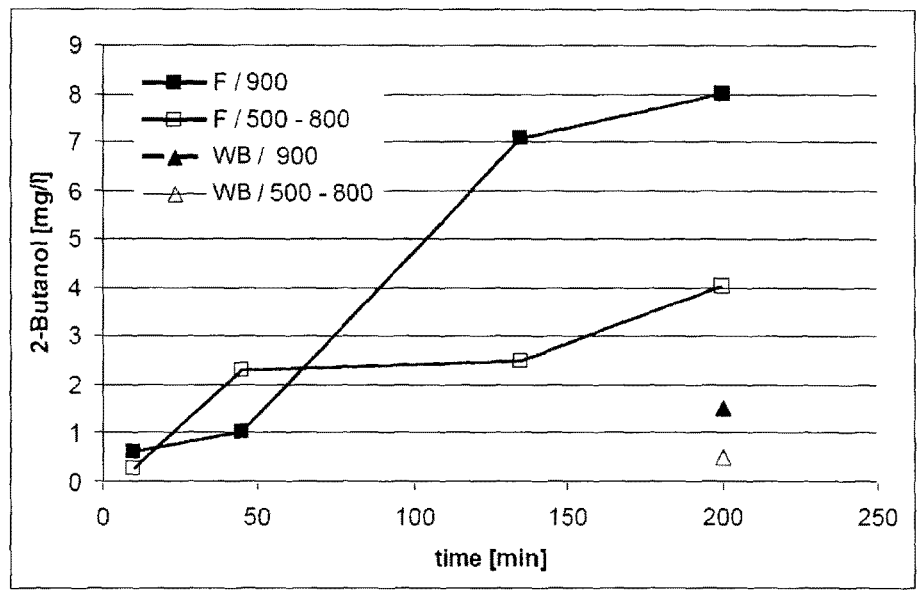
Figure 1:
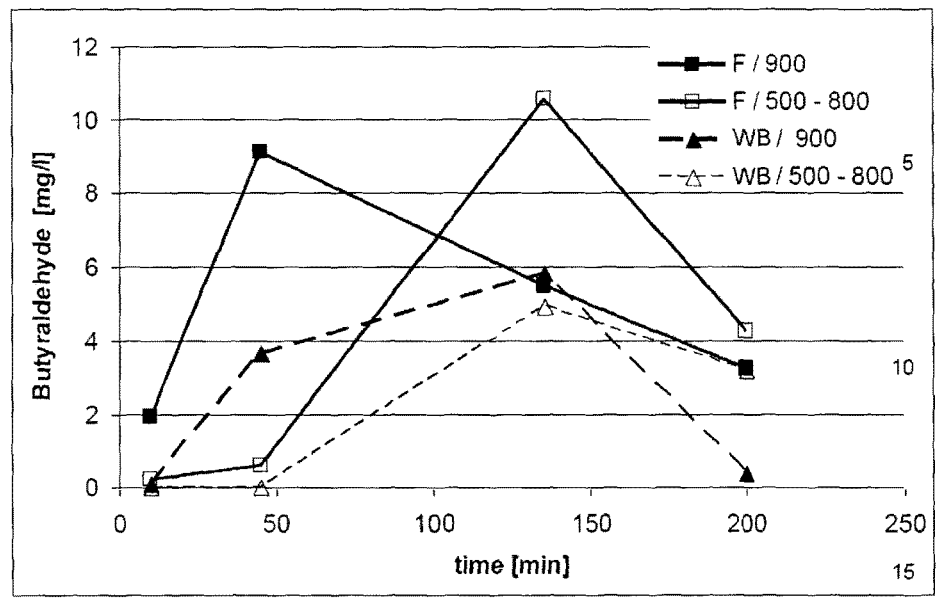
Figure 1:
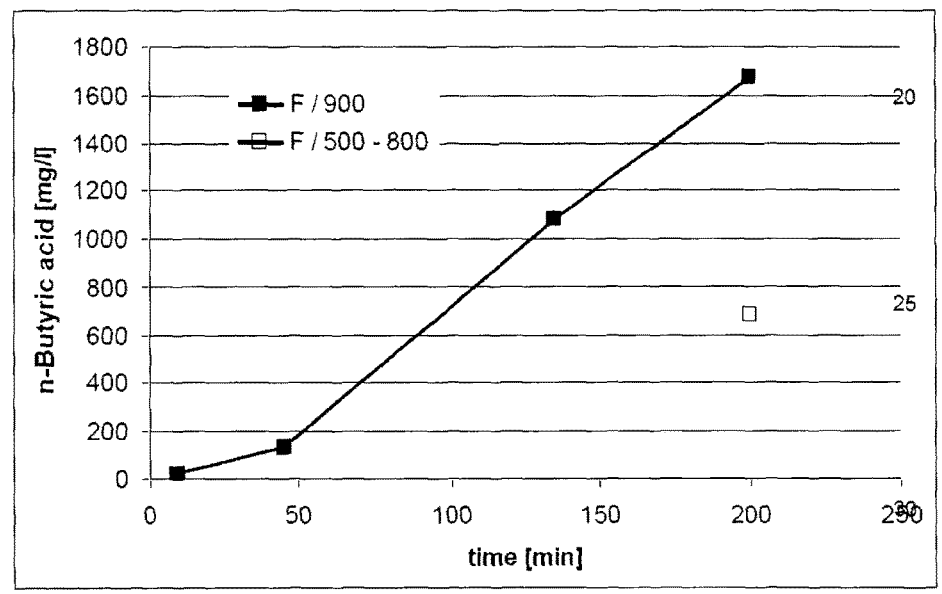

EXAMPLE 1: OXIDATION OF BUTANE BY *E. COLI* BY THE ALKBGT MONOOXYGENASE SYSTEM OF *P. PUTIDA* GPO1

100 µl of a glycerol cryoculture of *E. coli* BL21 pCOM10 (empty plasmid) and *E. coli* BL21 pBT10 (WO 2009/077461) are plated out on an LB agar plate with 50 µl of kanamycin and incubated at 37° C. for 24 h. The LB plates are prepared from 1 liter of a solution of yeast extract 5 g, peptone 10 g, NaCl 0.5 g, agar agar 15 g and kanamycin 50 µg. The pH is adjusted to 7.4 with 5% NH$_4$OH before autoclaving.

From these plates (for a conversion batch), 2×25 ml of LB broth (above solution without agar agar) with 50 µl of kanamycin in a 100 ml shaking flask with chicanes are inoculated with a full loop of an inoculating loop (capacity 10 µl). The cultures are incubated for 24 h at 37° C. and 200 rpm (amplitude 2.5 cm).

Each 25 ml of the culture broth are then used as inoculum in 75 ml of modified M9 medium (sterile filtered) with the following composition per liter: 15 g glucose, 6.79 g Na$_2$PO$_4$, 3 g KH$_2$PO$_4$, 0.5 g NaCl, 2 g NH$_4$Cl, 15 g yeast extract, 0.49 g MgSO$_4$*7H$_2$O, 1 ml TE and 50 µg kanamycin in 1000 ml shaking flasks. The trace element solution (TE) is made up per liter as follows: 36.5 g HCl 37%, 1.91 g $MnCl_2*4H_2O$, 1.87 g $ZnSO_4*7H_2O$, 0.84 g $Na-EDTA*2H_2O$, 0.3 g $H_3BO_3$, 0.25 g $Na_2MoO_4*2H_2O$, 4.7 g $CaCl_2*2H_2O$, 17.3 g $FeSO_4*7H_2O$ and 0.15 g $CuCl_2*2H_2O$). The pH is adjusted to 7.4 with 5% $NH_4OH$. In addition, 3 drops of autoclaved antifoam (Delamex) are added per flask.

The flasks are incubated for 2 h at 37° C. and 180 rpm (amplitude 2.5 cm). The temperature is then reduced to 25° C. The culture is induced after 0.5 hours at 25° C. with 0.4 mM DCPK. The culture is shaken for a further 16 hours at 25° C. and 180 rpm. A microscopic examination for monosepsis is then carried out.

The cultures are combined, filled into 50 ml falcon tubes and centrifuged at 10 000 g at 25° C. for 10 minutes. The supernatant is discarded. The pellets from 200 ml of culture are resuspended in 10 ml of conversion buffer. The conversion buffer consists of 70 mM $Na^+/K^+$ phosphate buffer, pH 7, adjusted with 1 M NaOH, containing 6.79 g $Na_2PO_4$, 3 g $KH_2PO_4$, 0.5 g NaCl, 0.49 g $MgSO_4*7H_2O$, 1 ml TE and 50 µg kanamycin or consists of 70 mM $(NH_4)H_2PO_4$ buffer, pH 7 containing 8 g $(NH_4)H_2PO_4$, 0.5 g NaCl, 0.49 g $MgSO_4*7H_2O$, 1 ml TE and 50 µg kanamycin per liter. The pH is adjusted in this case with 5% $NH_4OH$.

170 ml of buffer with ca. 3 drops of autoclaved antifoam (Delamex) are placed in a 300 ml fermenter. The fermenter is flushed with a gas mixture of 25% butane and 75% synthetic air from a gas cylinder at an initial pressure of 5 bar via a sintered glass aerator having a pore size of 0.2 µm at a flow rate of 25 l/h. The fermenter is heated to 25° C. in a water bath and stirred by means of a magnetic stirrer at 500 rpm for 2 hours, then at 800 rpm. The exhaust gas is passed through a wash bottle containing 150 ml of water.

The fermenter is inoculated with 10 ml of the resuspended pellets. The OD of both cultures is approx. 10. The reaction is initiated by addition of 1% by volume glucose. The pH may optionally be regulated or unregulated during the time course of the experiment. 10 ml samples are withdrawn from the fermenter and the wash bottle after 10, 45, 135 and 240 minutes. The reaction in the samples from the fermenter is stopped with 2 ml HCl. The fermenter samples are centrifuged at room temperature for 10 minutes at 10 000 g and the supernatant filtered through a 0.2 µm syringe filter unit. The samples are loaded into HPLC vials for analysis. The chromatographic analysis is conducted by HPLC-RID on an Agilent Technologies 1200 system. An Aminex HPX-87H column (300 mm×7.8 mm) was used. The system was operated using 10 mM $H_2SO_4$ as eluent at a flow rate of 0.6 ml/min and a column temperature of 40° C. Standards for all substances to be analyzed were prepared in ultra-pure water and measured under identical conditions. The evaluation was performed by comparison of retention times. In addition, a 2 ml sample is withdrawn from the fermenter at each sampling time point for the determination of pH, OD and glucose concentration. The pH is measured by an external pH-meter, the OD is determined spectrometrically at 600 nm and the glucose content with a biochemical analyzer (YSI Select 2700 from Kreienbaum).

Results

The results are shown in FIG. 1 a)-d). In the experiments with E. coli BL21 pCOM10 (empty plasmid), no oxidation of butane or 1-butanol occurred. In contrast, more applications of E. coli BL21pBT10 are found as oxidation products of n-butane: 1-butanol, butyric acid, 2-butanol, butyraldehyde, 1,4-butanediol (not quantifiable) and butyrolactone (traces).

The concentration of all oxidation products increases with the overall experimental time period. ca. 1 g/lh of glucose is consumed, the pH decreases from 7 to ca. 5.

EXAMPLE 2: INFLUENCE OF THE STIRRING SPEED (SUBSTANCE TRANSPORT LIMITING) ON THE OXIDATION OF N-BUTANE BY E. COLI WITH THE MONOOXYGENASE (ALKBGT) OF P. PUTIDA GPO1

The experiment is carried out analogously to example 1. The stirring speed is set to a constant 900 rpm from the start in a second batch. The OD is twice as high compared to example 1. The TE concentration is 15-fold. The final sampling is after 200 minutes.

Results

At a constant higher stirring speed, 1-butanol is formed more quickly in the fermenter (F) and reaches a maximum sooner. The concentration of 1-butanol in the wash bottles (WB) is at roughly identical low levels. The concentration of 2-butanol in the fermenter (F) increases with increasing stirrer speed over the entire experimental time course but remains low. 2-butanol is not detectable in the wash bottles until the end of the experimental time period. The concentration of butyraldehyde increases more rapidly with higher stirrer speeds, but is also driven off more rapidly since the vapour pressure is 113 hPa (20° C.). Butyraldehyde is only qualitatively, but not quantitatively, detectable.

At lower stirrer speeds, n-butyric acid is not formed until the end of the experimental time period. At higher stirrer speeds, the concentration increases continuously. n-Butyric acid cannot be detected in the wash bottles.

EXAMPLE 3: INFLUENCE OF THE BIOMASS CONCENTRATION ON THE OXIDATION OF N-BUTANE BY E. COLI WITH THE MONOOXYGENASE (ALKBGT) OF P. PUTIDA GPO1

The experiment is carried out analogously to example 1. The stirrer speed is constant at 900 rpm, the TE concentration is respectively 15-fold. 1× means an OD of ca. 10, 2× corresponds to 20.

Results

Figure 2:
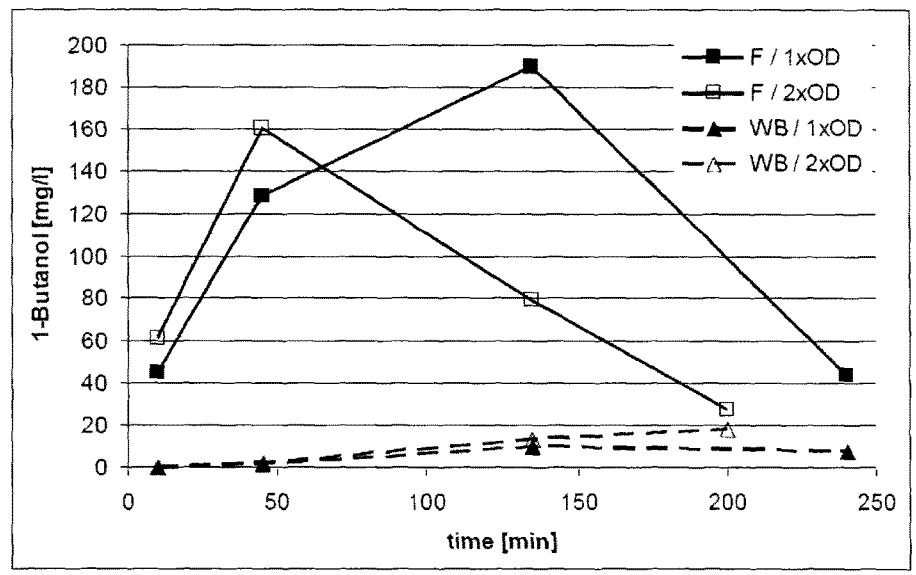
Figure 2:
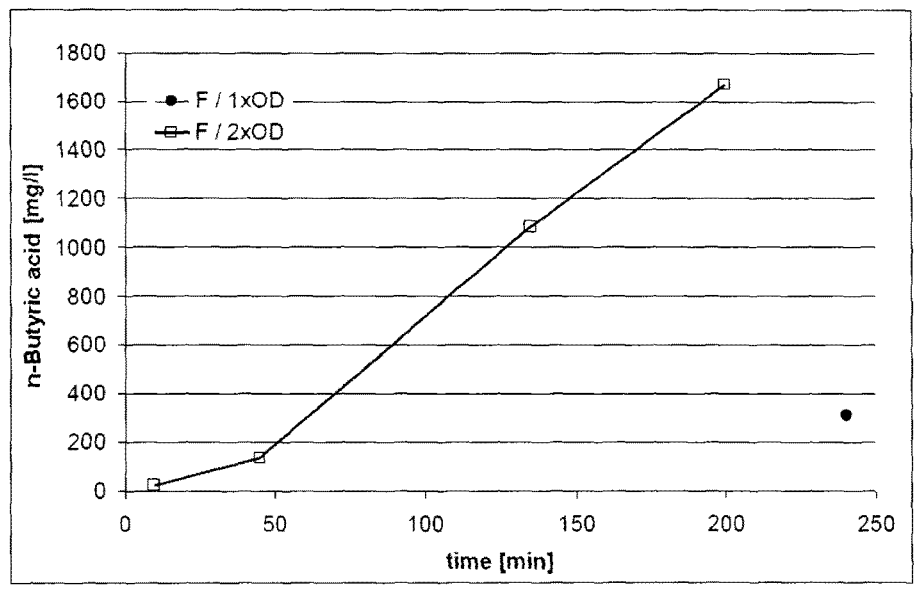

The results are shown in FIGS. 2 a) and b). The maximum concentration is reached at an earlier experimental time point at twice the OD. 1-Butanol is also more rapidly converted.

Butyric acid can only be detected in the fermenter (F), not in the wash bottles. At twice the OD, the formation of butyric acid already begins at the start of the conversion. At one-fold OD, butyric acid cannot be detected under these conditions until after 240 minutes. The concentration is approximately 18% of the maximum concentration at twice the OD.

EXAMPLE 4: INFLUENCE OF THE TE CONCENTRATION ON THE OXIDATION OF N-BUTANE BY E. COLI WITH THE MONOOXYGENASE (ALKBGT) OF P. PUTIDA GPO1

The experiment is carried out analogously to example 1. The stirrer speed is constant at 900 rpm. The strain used is E. coli W3110 pBT10. The concentration of TE is 1 ml/l of buffer (1×) or 15 ml/l of buffer (15×). In the experiment with the 15-fold concentration, an additional 30 mg/l MOPS are added.

Results

Figure 3:
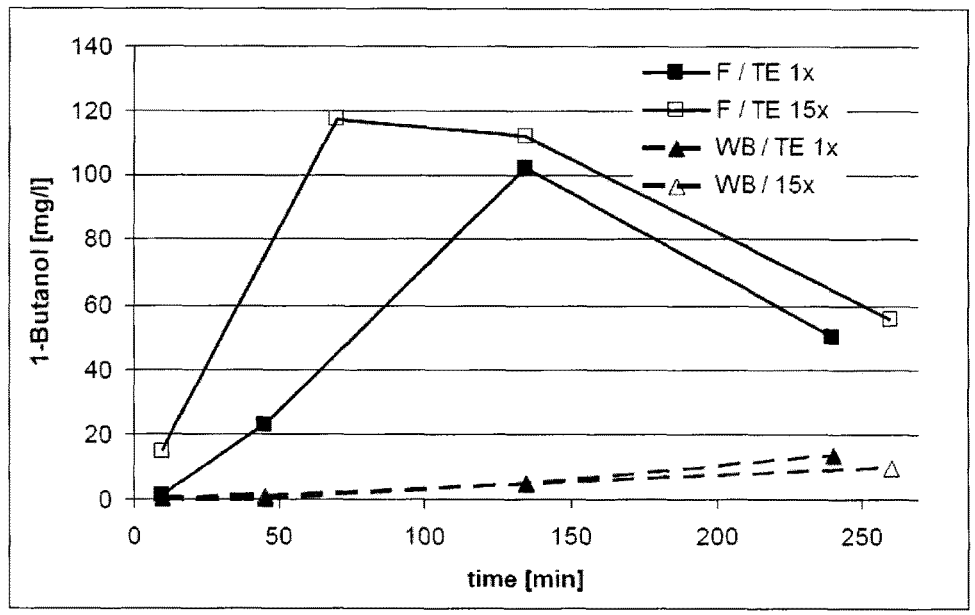
Figure 3:
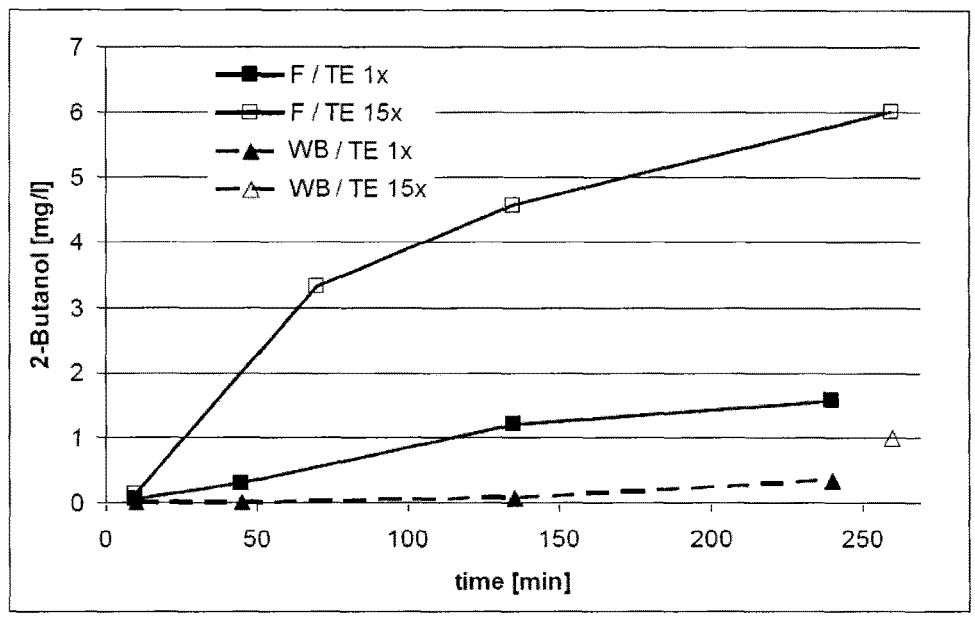
Figure 3:
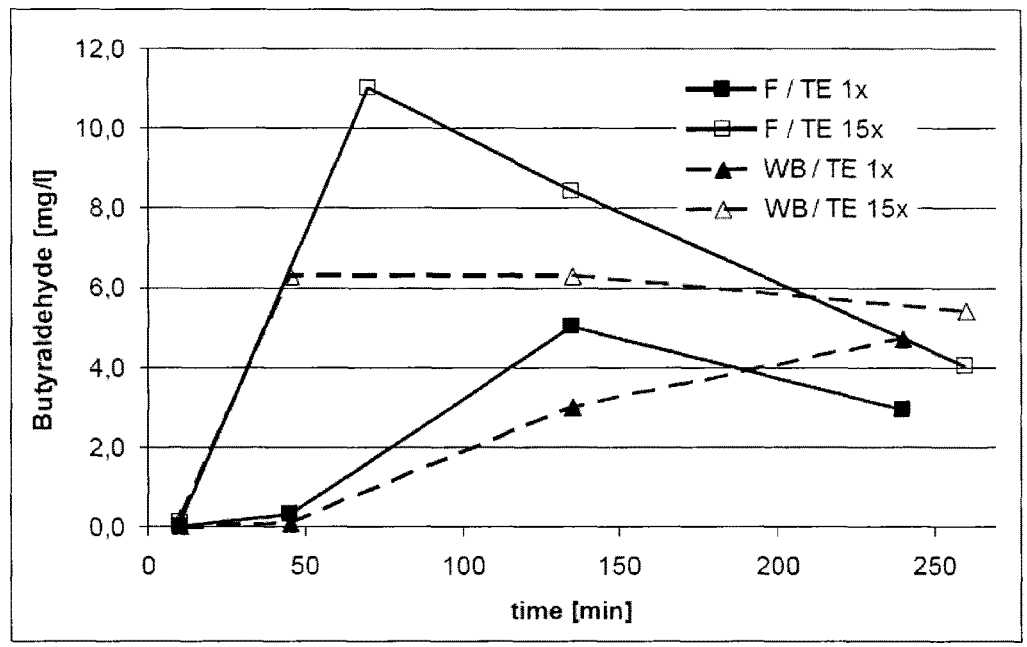
Figure 3:
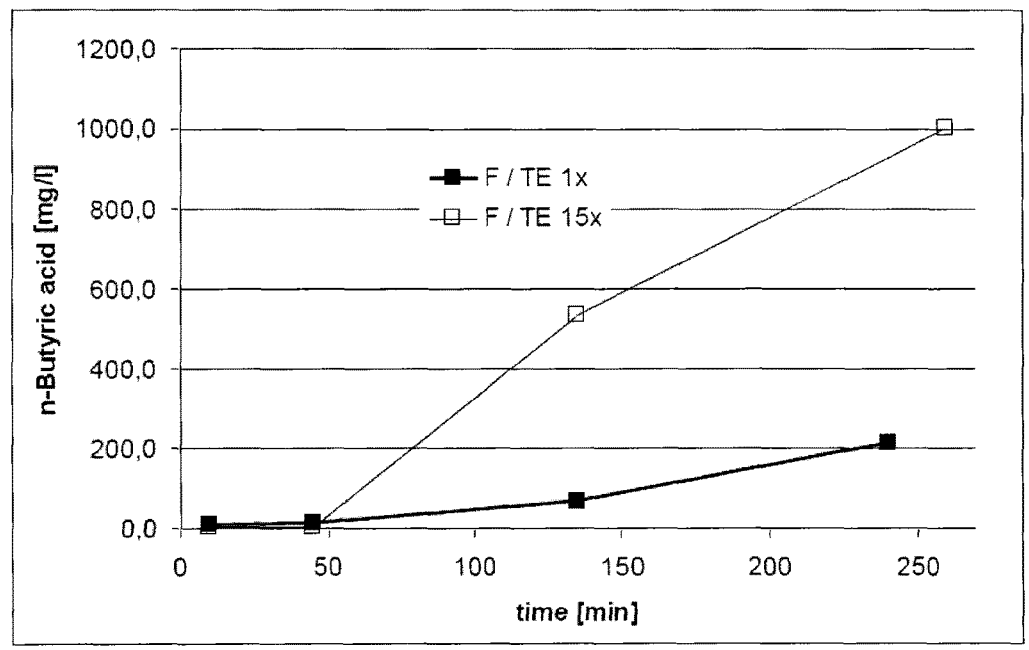

The results are shown in FIGS. 3 a)-d). In the 15-fold TE concentrations, all oxidation products are formed more rapidly and in higher concentrations.

EXAMPLE 5: COMPARISON OF THE STRAINS E. CON BL21 AND E. CON W3110 WITH THE MONOOXYGENASE (ALKBGT) OF P. PUTIDA GPO1

The experiment is carried out analogously to Example 1 with fixed stirrer speed of 900 rpm. The TE concentration is 15 ml/l of conversion buffer.

Results

Figure 4:
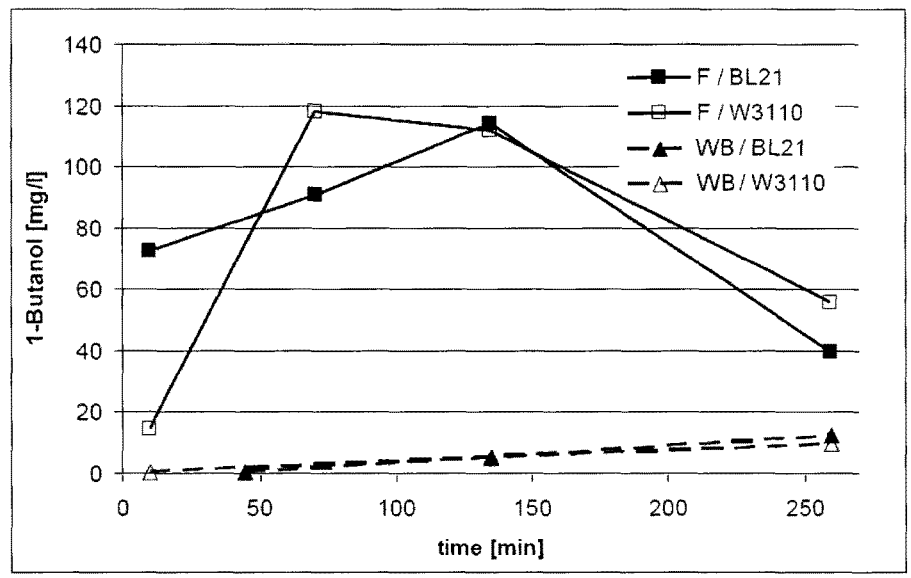
Figure 4:
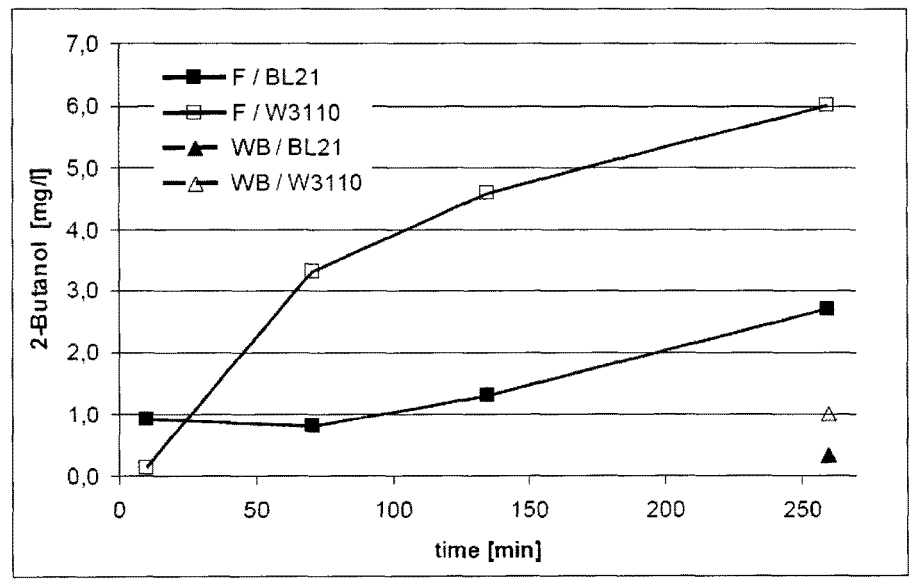
Figure 4:
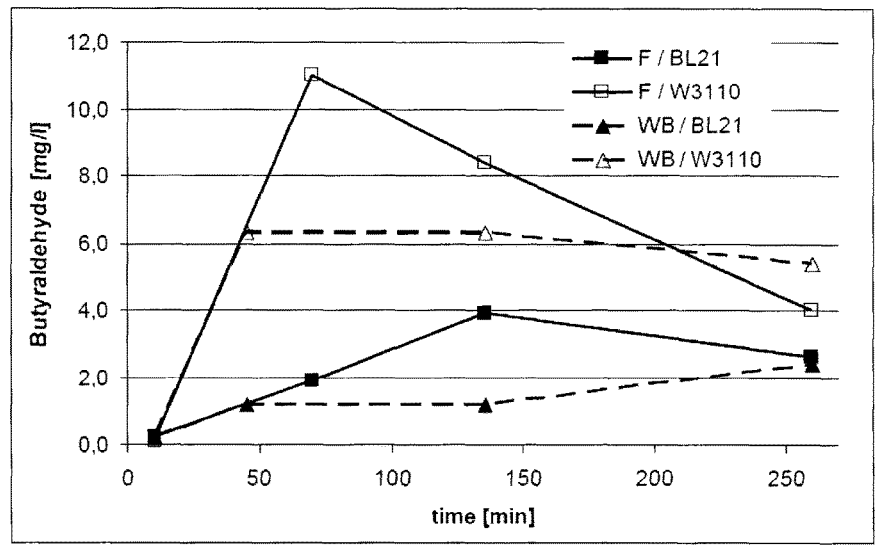
Figure 4:
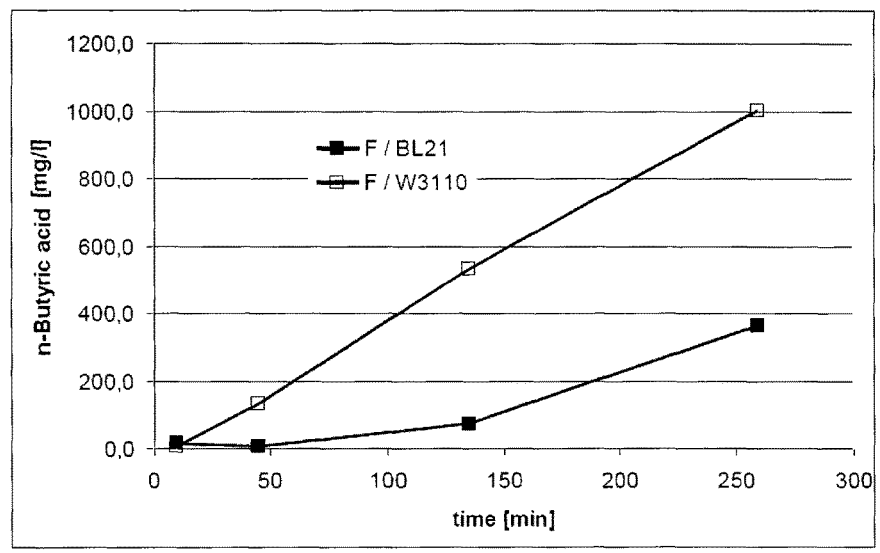

The results are shown in FIGS. 4 a)-d). The E. coli W3110 pBT10 strain forms all oxidation products more rapidly and in higher concentrations than the E. coli BL21 pBT10 strain.

EXAMPLE 6: OXIDATION OF ISOBUTANE BY E. COLI WITH THE MONOOXYGENASE (ALKBGT) OF P. PUTIDA GPO1

The workflow is carried out analogously to example 1. Only the E. coli W3110 pBT10 strain is used. The conversion buffer consists of 70 mM $Na^+/K^+$ phosphate buffer, pH7, adjusted with 5% $NH_4OH$, containing 6.79 g $Na_2PO_4$, 3 g $KH_2PO_4$, 0.5 g NaCl, 0.49 g $MgSO_4*7H_2O$, 15 ml TE and 50 μg kanamycin per liter.

The gas flushing is carried out as in example 1 but with a mixture of 25% isobutane and 75% synthetic air.

Results

Figure 5:
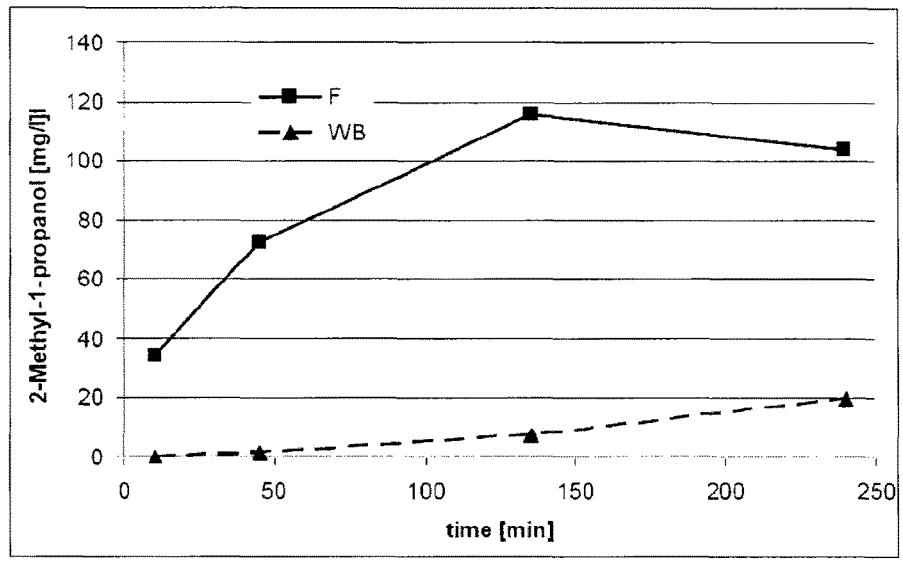
Figure 5:
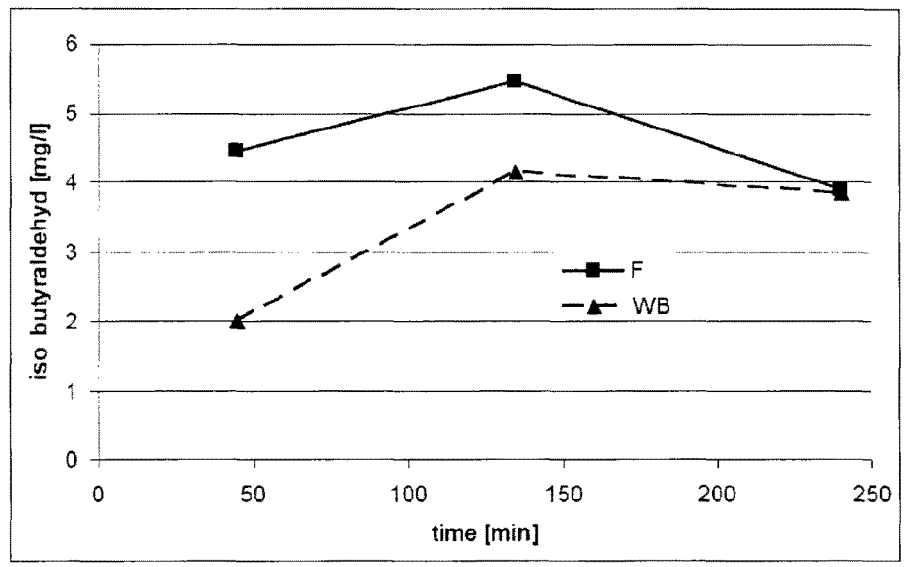
Figure 5:
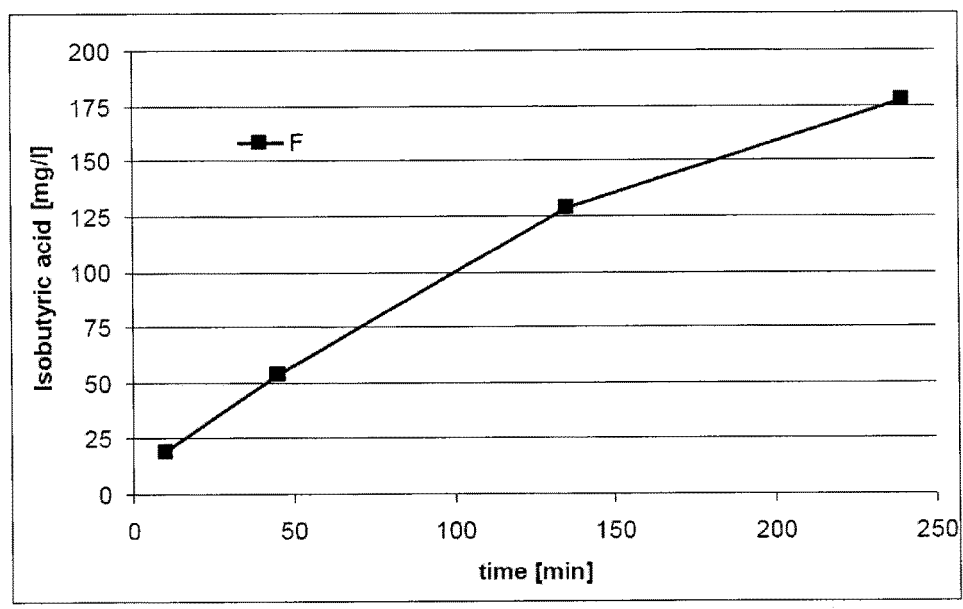
Figure 6:
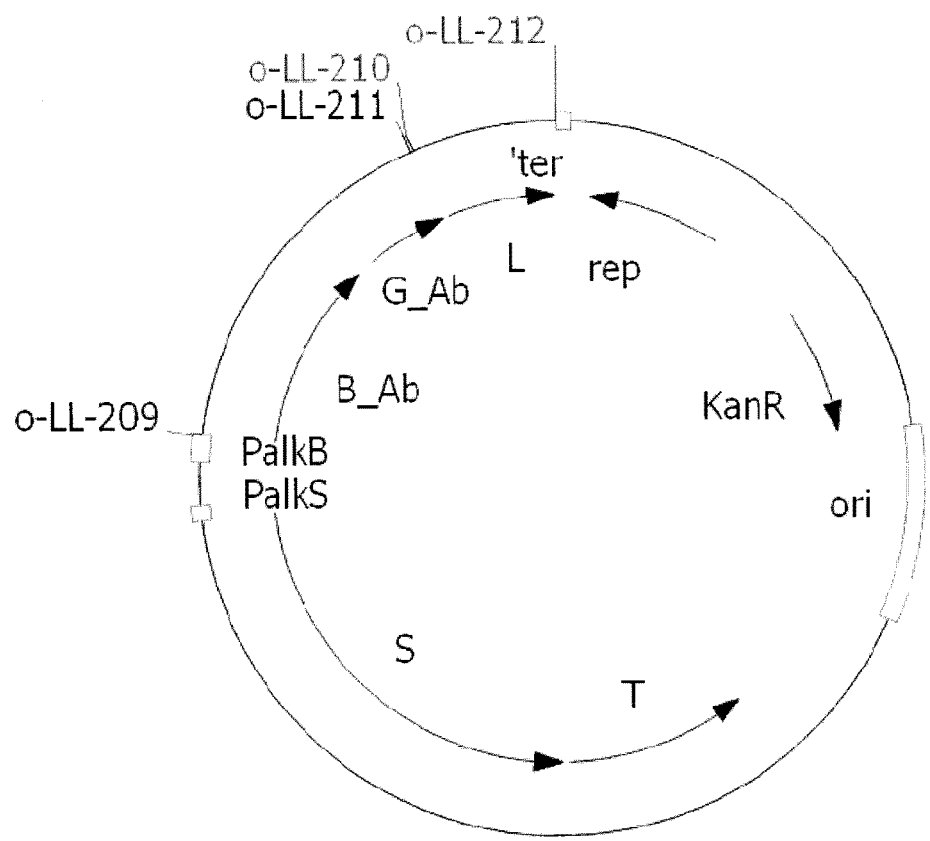
FIG. 6 shows schematically the cloned vector p-LL-30 for example 7.

The results are shown in FIGS. 5 a)-c). The oxidation products of isobutane found are isobutanol, isobutyric acid, tert-butanol and isobutyraldehyde.

EXAMPLE 7: OXIDATION OF BUTANE BY E. COLI WITH THE ALKBG MONOOXYGENASE SYSTEM OF ALCANIVORAX BORKUMENSIS

The strain used for the oxidation comprises a plasmid with the genetic information for the alkBG monooxygenase from Alcanivorax borkumensis SK2 (Databank code CAL18155.1 and CAL18156.1). The genetic information for alkST, alkL, and the promoters for alkS and alkB originate from Pseudomonas putida GPo1.

Cloning of the Target Vector

For multiplication, the 2× Phusion HF Master Mix from New England Biolabs (NEB, M0531S) was used according to the manufacturer's instructions. Depending on the degree of purity, the vectors and PCR products were purified directly on a column (QiaQuick PCR Purification Kit, Qiagen, Hilden) or purified on an agarose gel and extracted (QiaQuick Gel Extraction Kit, Qiagen, Hilden). PCR, agarose gel electrophoresis, ethidium bromide staining of the DNA and determination of PCR fragment sizes were carried out in the manner known to the skilled worker. It was possible in both cases to provide PCR fragments of the expected size. For the PCR, the primers with the stated sequences SEQ ID NO 1, 2, 3, and 4 were used.

Figure 7:
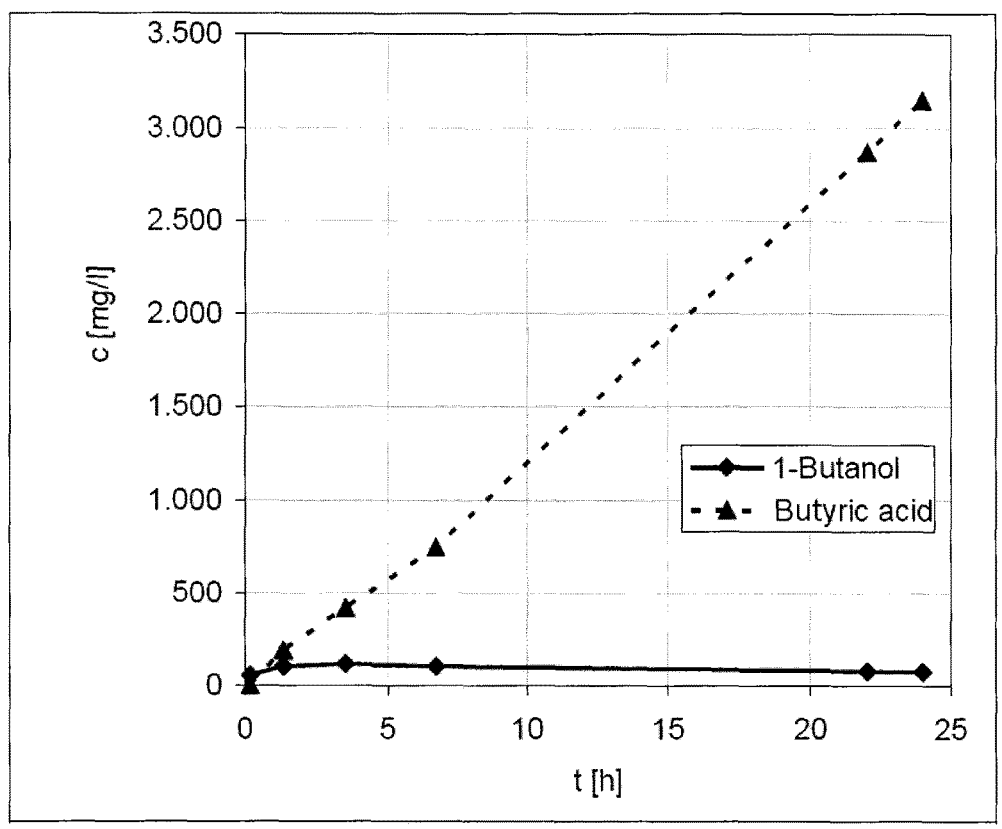
FIG. 7 shows the oxidation of butane by *E. coli* with the alkBG monooxygenase system of *Alcanivorax borkumensis*, as carried out in example 7.

The purified PCR products were cloned into the EcoRI-HF+Ac/l-cut vector pBT10_alkL after gel purification by means of recombination using the In-Fusion HD Cloning Kit according to the manufacturer's instructions (Clontech Laboratories Inc., Mountain View, Calif., USA). Chemically competent E. coli DH10□(New England Biolabs, Frankfurt) were transformed in the manner known to the skilled worker. Correct insertion of the target sequences was checked by restriction analysis and authenticity of the sequences introduced was confirmed by DNA sequencing. The resulting vector was referred to as p-LL-30 (FIG. 7). The sequence of the vector is stated in the sequence protocol under SEQ ID NO 5.

Donor Organisms and Donated Genes:

Pseudomonas putida GPo1
    ACCESSION AJ245436
    alkB gene
    integral membrane non-heme iron monooxygenase
    protein_id="CAB54050.1
    alkF gene
    rubredoxin 1
    protein_id="CAB54051.1
    alkG gene
    rubredoxin 2
    protein_id="CAB54052.1
        alkH gene
    aldehyde dehydrogenase
    ACCESSION AJ245436
    alkT gene
    rubredoxin reductase
        protein_id="CAB54063.1
    alkL gene
    outer membrane protein
    protein_id="CAB54056.1
    alkS gene
    Expression regulator
    protein_id="CAB54064.1"

Alcanivorax borkumensis 1
    alkB_Ab gene
    alkane 1-monooxygenase
    CAL18155.1
    alkG_Ab gene
    rubredoxin
    CAL18156.1

The target vector was cloned into E. coli W3110 in a manner known to the skilled worker. The resulting strain was referred to as E. coli W3110 AN-S-LL-16.

Cell Culture and Biotransformation:

100 μl of a glycerol cryoculture E. coli W3110 EN-S-LL-16 are plated out on an LB agar plate with 50 μl of kanamycin and incubated for 24 h at 37° C. The LB plates are prepared from 1 liter of a solution of yeast extract 5 g, peptone 10 g, NaCl 0.5 g, agar agar 15 g and kanamycin 50 μg.

From these plates, 3×25 ml of LB broth (above solution without agar agar) with 50 μl of kanamycin in a 100 ml shaking flask with chicanes are inoculated with a single colony from the plate. The cultures are incubated for 24 h at 37° C. and 200 rpm (amplitude 2.5 cm).

Each 25 ml of the culture broth are then used as inoculum in 175 ml of modified M9 medium with the following composition per liter: 15 g glucose, 6.79 g $Na_2PO_4$, 3 g $KH_2PO_4$, 0.5 g NaCl, 2 g $NH_4Cl$, 15 g yeast extract, 0.49 g $MgSO_4*7H_2O$, 1 ml TE and 50 μg kanamycin in 1000 ml shaking flasks. The trace element solution (TE) is made up per liter as follows: 36.5 g HCl 37%, 1.91 g $MnCl_2*4H_2O$, 1.87 g $ZnSO_4*7H_2O$, 0.84 g $Na-EDTA*2H_2O$, 0.3 g $H_3BO_3$, 0.25 g $Na_2MoO_4*2H_2O$, 4.7 g $CaCl_2*2H_2O$, 17.3 g $FeSO_4*7H_2O$ and 0.15 g $CuCl_2*2H_2O$). The pH is adjusted to 7.4 with 5% $NH_4OH$. In addition, 3 drops of autoclaved antifoam (Delamex) are added per flask.

The flasks are incubated for 2 h at 37° C. and 180 rpm (amplitude 2.5 cm). The temperature is then reduced to 25° C. The culture is induced after 0.5 hours at 25° C. with 0.4 mM DCPK. The culture is shaken for a further 16 hours at 25° C. and 180 rpm.

The cultures are combined, filled into 50 ml falcon tubes and centrifuged at 10 000 g at 25° C. for 10 minutes. The supernatant is discarded. The pellets from 600 ml of culture are resuspended in 30 ml of conversion buffer. The conversion buffer consists of 70 mM ammonium phosphate buffer, pH 7 containing 8 g $(NH_4)H_2PO_4$, 0.5 g NaCl, 0.49 g $MgSO_4*7H_2O$, 1 ml TE and 50 µg kanamycin per liter. The pH is adjusted with 25% ammonia solution.

150 ml of buffer with ca. 3 drops of autoclaved antifoam (Delamex) are placed in a 300 ml fermenter. The fermenter is flushed with a gas mixture of 25% butane and 75% synthetic air via a sintered glass aerator having a pore size of 0.2 µm at a flow rate of 6.5 $I_N$/h. The fermenter is heated to 30° C. in a water bath and stirred by means of a magnetic stirrer at 900 rpm. The exhaust gas is passed through a wash bottle containing 150 ml of water.

The fermenter is inoculated with the resuspended preculture pellets. The OD600 is approx. 15. The pH is regulated to 7.0 with 5% ammonia solution. The glucose feed rate is 1 g/lh. 5 ml samples are removed at various time points from the fermenter and the wash bottle. The fermenter samples are centrifuged at room temperature for 10 minutes at 10 000 g and the supernatant filtered through a 0.2 µm syringe filter unit. The samples are loaded into HPLC vials for analysis. The chromatographic analysis is conducted by HPLC-RID on an Agilent Technologies 1200 system. An Aminex HPX-87H column (300 mm×7.8 mm) is used. The system is operated using 10 mM $H_2SO_4$ as eluent at a flow rate of 0.6 ml/min and a column temperature of 40° C. Standards for all substances to be analyzed are prepared in ultra-pure water and measured under identical conditions. The evaluation is performed by comparison of retention times. In addition, a 2 ml sample is withdrawn from the fermenter at each sampling time point for the determination of pH, OD and glucose concentration. The pH is measured by an external pH-meter, the OD is determined spectrometrically at 600 nm and the glucose content with a biochemical analyzer (YSI Select 2700 from Kreienbaum). The results are summarized in FIG. 7.

BIBLIOGRAPHY

A. Cornish-Bowden (1995), Fundamentals of Enzyme Kinetics, Portland Press Limited, 1995
DE 60216245 (2007): Functional Display of Polypeptides
Sambrook/Fritsch/Maniatis (1989): Molecular Cloning: A Laboratory Manual, Cold Spring Harbor Laboratory Press, $2^{nd}$ edition
Fuchs/Schlegel (2007) Allgemeine Mikrobiologie, 2008, Georg Thieme Verlag
EP 98137 (1984) A microbiological process for the oxidation of alkanes, vinyl compounds and secondary alcohols
WO 2009/077461: ω-Aminocarbonsäuren oder ihre Lactame, herstellende, rekombinante Zellen
A. Lesk (2008), Introduction to bioinformatics, 3rd edition
F. M. Ausubel (1995), Current Protocols in Molecular Biology. John Wiley & Sons, Inc.
C Grant, J M Woodley, F Baganz (2011): Enzyme and Microbial Technology 48, 480-486

The invention claimed is:

1. A method for preparing a mixture of oxidation products of a $C_1$-$C_5$ alkane comprising:
   contacting a $C_1$-$C_5$ alkane with oxygen in the presence of an AlkB oxidoreductase, wherein the amino acid sequence of said AlkB oxidoreductase is at least 90% identical to that of the AlkB oxidoreductase of *Pseudomonas putida* described by SEQ ID NO: 6 for a time and under conditions sufficient to oxidize the alkane to a corresponding alcohol and carboxylic acid; and
   recovering a mixture of oxidation products where the ratio of carboxylic acid to alcohol is greater than 1:1.

2. The method according to claim 1, wherein the alkane is a $C_1$-$C_4$ alkane.

3. The method according to claim 1, wherein the $C_1$ to $C_5$ alkane is a branched alkane.

4. The method according to claim 1, wherein the AlkB oxidoreductase is AlkB from *Pseudomonas putida* GPO1.

5. The method according to claim 1, wherein the AlkB oxidoreductase is in the form of a whole-cell catalyst.

6. The method according to claim 1, wherein the AlkB oxidoreductase is in the form of a purified polypeptide.

7. The method according to claim 1, comprising recovering a mixture of oxidation products where the ratio of carboxylic acid to alcohol in the oxidation products is greater than 5:1.

8. The method according to claim 3, wherein the alkane is a $C_4$ or $C_5$ alkane.

9. The method according to claim 1, comprising recovering a mixture of oxidation products where the ratio of carboxylic acid to alcohol is greater than 12:1.

10. The method according to claim 1, comprising recovering a mixture of oxidation products where the ratio of carboxylic acid to alcohol is greater than 20:1.

11. The method according to claim 1, comprising recovering a mixture of oxidation products where the ratio of carboxylic acid to alcohol is greater than 40:1.

12. The method according to claim 1, wherein the $C_1$-$C_5$ alkane is oxidized predominantly into a carboxylic acid.

13. The method according to claim 1, wherein the $C_1$-$C_5$ alkane is oxidized at a terminal carbon atom.

14. A method for preparing a mixture of oxidation products of an alkane comprising:
    contacting a $C_1$-$C_5$ alkane with oxygen and with an AlkB oxidoreductase and optionally AlkG or AlkT enzyme(s),
    wherein the amino acid sequence of said AlkB oxidoreductase is at least 90% identical to that of the alkB oxidoreductase of *Pseudomonas putida* described by SEQ ID NO: 6, the amino acid sequence of AlkG is at least 90% identical to the AlkG sequence described by SEQ ID NO: 7, and the amino acid sequence of AlkT is at least 90% identical to the AlkT sequence described by SEQ ID NO: 8; and
    recovering a mixture of oxidation products where the ratio of carboxylic acid to alcohol is greater than 1:1.

15. The method according to claim 14, wherein the alkB oxidoreductase is expressed along with an AlkG that has a sequence that is at least 90% identical to the AlkG sequence described by SEQ ID NO: 7 and an AlkT that has a sequence that is at least 90% identical to the AlkT sequence described by SEQ ID NO: 8.

16. The method according to claim 14, wherein the alkane is contacted with oxygen and with a *Pseudomonas putida* enzyme consisting of an alkB oxidoreductase that is at least 90% identical to that of the AlkB oxidoreductase of *Pseudomonas putida* described by SEQ ID NO: 6.

17. The method according to claim 14, wherein said alkB oxidoreductase is contained within a whole cell catalyst or a crude lysate thereof.

18. The method according to claim 14, wherein said alkB oxidoreductase is in a non-cellular, purified form that when resolved on an SDS gel represents at least 99% of the visible proteins.

19. The method of claim 1, wherein the alkB oxidoreductase is a purified AlkB oxidoreductase and is in either soluble or immobilized form.

20. The method of claim 1, wherein the AlkB oxidoreductase is a form of an engineered recombinant whole cell catalyst that expresses more AlkB oxidoreductase than a corresponding non-recombinant whole cell catalyst, wherein said engineered recombinant whole cell catalyst contains an exogenous nucleic acid sequence encoding an AlkB oxidoreductase on a plasmid or integrated into its genome.

* * * * *